United States Patent [19]
Caput et al.

[11] Patent Number: 6,001,649
[45] Date of Patent: Dec. 14, 1999

[54] CHEMOKINE NC28 (MONOCYTE CHEMOTACTIC PROTEIN-3, MCP-3) POLYPEPTIDES AND THEIR RECOMBINANT PRODUCTION

[75] Inventors: Daniel Caput, Toulouse; Pascual Ferrara, VilleFranche de Lauragais; Brigitte Miloux, Montgiscard; Adrian Minty, Mervilla; Natalio Vita, Saint Orens, all of France

[73] Assignee: Societe Anonyme: Elf Sanofi, Paris, France

[21] Appl. No.: 07/927,391

[22] PCT Filed: Nov. 29, 1990

[86] PCT No.: PCT/FR91/00949

§ 371 Date: Sep. 29, 1992

§ 102(e) Date: Sep. 29, 1992

[87] PCT Pub. No.: WO92/09629

PCT Pub. Date: Jun. 11, 1992

[30] Foreign Application Priority Data

Nov. 29, 1990 [FR] France .................... 90 14961

[51] Int. Cl.⁶ ............... C12N 15/19; C07K 14/52
[52] U.S. Cl. ............. 435/365.1; 435/69.5; 435/320.1; 435/325; 435/360; 435/254.2; 530/351; 530/327; 530/326; 530/325; 530/324; 536/23.51; 514/2; 514/14; 514/13; 514/12; 424/85.1
[58] Field of Search ................... 530/350, 351, 530/327, 326, 325, 324; 536/23.5, 23.51; 435/69.1, 69.5, 240.1, 320.1, 325, 360, 365.1, 254.2; 514/2, 14, 13, 12; 424/85.1

[56] References Cited

FOREIGN PATENT DOCUMENTS

90/07863  7/1990  WIPO .
90/08777  9/1990  WIPO .

OTHER PUBLICATIONS

Chang, H. C., et al. (1989) Int. Immunol. 1: 388–97.

Oppenheim, J. J., et al. (1991) Ann. Rev. Immunol. 9: 617–48.

Van Damme, J., et al. (1992) J. Exp. Med. 176: 59–65.

Ferrara et al. "Characterization of Recombinant Glycosylated Human Interleukin–2 Produced By A Recombinant Plasmid . . . ", *FEBS Ltrs.*, 226(1): 47–52 (1987).

Singh et al. "Synergism Between Human Monocyte Chemotactic and Activating Factor and Bacterial . . . ", *J. Immun.*, 151(5): 2786–2793 (1993).

Minty et al. "Molecular Cloning of the MCP–3 Chemokine Gene and Regulation of its Expression", *Eur. Cytokine Netw.*, 4(2): 99–110 (1993).

Rollins et al. "Suppression of Tumor Formation in Vivo by Expression of the JE Gene in Malignant Cells", *Mol. Cell. Biol.*, 11(6): 3125–3131 (1991).

Tepper et al. "Murine Interleukin–4 Displays Potent Anti–Tumor Activity In Vivo", *Cell*, 57: 503–512 (1989).

*Primary Examiner*—David L. Fitzgerald
*Attorney, Agent, or Firm*—Foley & Lardner

[57] ABSTRACT

A new chemotactic cytokine, NC28 or Monocyte Chemotactic Protein-3 (MCP-3), is provided. Fragments of the cytokine comprising its 13 C-terminal amino acids also exhibit chemotactic activity. The polypeptides may be used as anticancer agents or immunomodulators. DNA encoding the NC28/MCP-3 polypeptides, as well as corresponding vectors and recombinant expression systems, are also provided.

31 Claims, 12 Drawing Sheets

FIG. 1b-1

SITE BINDING TO HindIII

```
       1  AGCTGGCCTCGCATCTCTCCTTCACGCGCCCGCCGCCCTACCTGAGGCCGCCATCCACGCC  60
          ----------+---------+---------+---------+---------+---------+
          TCGACCGGAGCGTAGAGAGGAAGTGCGCGGGCGGCGGGATGGACTCCGGCGGTAGGTGCGG

61  GGTGAGTCGCGGTTCTGCCGCCCTCCCGCCCTGTGGTGCCTCCTGAACTGCGTCCGCGTCTA 120
          ----------+---------+---------+---------+---------+---------+
          CCACTCAGCGCCAAGACGGCGGGAGGGCGGGACACCACGGAGGACTTGACGCAGGCGCAGAT

121  GGTAGGCTCCAAGGGAGCCGGACAAAGGCCCGGTCTCGACCTGAGCTCTAAACTTACCTA  180
          ----------+---------+---------+---------+---------+---------+
          CCATCCGAGGTTCCCTCGGCCTGTTTCCGGGCCAGAGCTGGACTCGAGATTTGAATGGAT

181  GACTCAGCCGGCTCTCCACGCTTTGCCTGACCCTGCTTGCTCAACTCTACGTCTTTGTTT  240
          ----------+---------+---------+---------+---------+---------+
          CTGAGTCGGCCGAGAGGTGCGAAACGGACTGGGACGAACGAGTTGAGATGCAGAAACAAA
```

FIG. 1b-2

```
     CGTTTCTGTTCTGCGCCGTTACAACTTCAAGGTATGCGCTGGGACCCTGGCAGGCGGCAT
20 241 ------+---------+---------+---------+---------+---------+ +300
     GCAAAGACAAGACGCGGCAATGTTGAAGTTCCATACGCGACCCTGGACCGTCCGCCCGTA

CTGGGACCCCCTAGGAAGGGCTTGGGGGTCCTCGTGCCCAAGGCAGGGAACATAGTGGTCC
25 301 ------+---------+---------+---------+---------+---------+ +360
     GACCCTGGGGATCCTTCCCGAACCCCCAGGAGCACGGGTTCCGTCCCTTGTATCACCAGG

CAGGAAGGGGAGCAGAGGCAGAGGCATCAGGGTGTCCACTTTGTCTCCGCAGCTCCTGAGCCTGCA
30 361 ------+---------+---------+---------+---------+---------+ +420
     GTCCTTCCCCCTCGTCTCCGTAGTCCCACAGGTGAAACAGAGGCGTCGAGGACTCGGACGT
```

```
   GA
   ---
   CTTCGA ▲
          HindIII
```

FIG. 2a

```
     AGCAGAGGGCTGAGACCAAACCTCCAATTCTCATGTGGAAGCCCATGCCC                     58
                                      MetTrpLysProMetPro                    6
 59  TCACCCTCCAACATGAAAGCCTCTGCAGCACTTCTGTGTCTGCTGCTCACAGCAGCTGCT          118
  7  SerProSerAsnMetLysAlaSerAlaAlaLeuLeuCysLeuLeuLeuThrAlaAlaAla           26
119  TTCAGCCCCCAGGGCTTGCTCAGCCAGTTGGGATTAATACTTCAACTACCTGCTGCTAC           178
 27  PheSerProGlnGlyLeuAlaGlnProValGlyLeuIleLeuGlnLeuProAlaAlaThr           46
     (should read) PheSerProGlnGlyLeuAlaGlnProValGlyLeuIleLeuGlnLeuProCysCysTyr
179  AGATTTATCAATAAGAAATCCCTAAGCAGAGGCTGGAGAGCTACAGAAGGACCACCAGT           238
 47  ArgPheIleAsnLysLysIleProLysGlnArgLeuGluSerTyrArgArgThrThrSer           66
239  AGCCACTGTCCCCGGGAAGCTGTAATCTTCAAGACCAAACTGGACAAGGAGATCTGTGCT          298
 67  SerHisCysProArgGluAlaValIlePheLysThrLysLeuAspLysGluIleCysAla           86
299  GACCCCACAGAAGTGGGTCCAGGACTTTATGAAGCACCTGGACAAGAAAACCCAAACT           358
 87  AspProThrGlnLysTrpValGlnAspPheMetLysHisLeuAspLysLysThrGlnThr          106
359  CCAAAGCTTTGAACATTCATGACTGAACTAAAAAACAAGCCATGACTTGAGAAACAAATAA         418
107  ProLysLeu                                                             126
```

FIG. 2b

```
419  TTTGTATACCCTGTCCCTTTCTCAGAGTGGTTCTGAGATTATTTAATCTAATTCTAAGGA   478
479  ATATGAGCTTTATGTAATAAATCATGGTTTTTCTTAGTAGATTTTAAAAGTTATT       538
539  AATATTTTAATTTAATCTTCCATGGATTTGGTGGGTTTGAACATAAAGCCTTGGATGT    598
599  ATATGTCATCTCAGTGCTGTAAAAACTGTGGGATGCTCCTCCCCTTCTCTACCTCATGGGG 658
659  GTATTGTATAAGTCCCTTGCAAGAATCAGTGCAAAGATTTGCTTTAATTGTTAAGATATGA 718
719  TGTCCCTATGGAAGCATATTGTTATTATATAATTACATATTTGCATATGTATGACTCCCA  778
779  AATTTTCACATAAAATAGATTTTTGTAAAAAAAAA.......  820
```

```
  1 MetTrpLysProMetProSerAsn MetLysAlaSerAlaAlaLeuLeuCysLeu  20
                             — — — — — — — — — — — — — — —
  1 ........................ MetLysValSerAlaAlaLeuLeuCysLeu  10

21 LeuLeuThrAlaAlaAlaPheSerProGln GlyLeuAlaGlnProValGlyIleAsnThr  40
    — — — — — — — — —            — — — — —         —   —
 11 LeuLeuIleAlaAlaAlaThrPheIleProGln GlyLeuAlaGlnProAspAlaIleAsnAla  30

41 SerThrThrCysCysTyrArgPheIleAsn LysLysIleProLysGlnArgLeuGluSer  60
      —   — — — — —   —   — —     —   — — —   —   — — — —
 31 ProValThrCysCysTyrAsnPheThrAsn ArgLysIleSerValGlnArgLeuAlaSer  50

61 TyrArgArgThrThrSerSerHisCysPro ArgGluAlaValIlePheLysThrLysLeu  80
    — — — —     — — —   — —       —   — — — — — — — —   —
 51 TyrArgArgIleThrSerSerLysCysPro LysGluAlaValIlePheLysThrIleVal  70

81 AspLysGluIleCysAlaAspProThrGln LysTrpValGlnAspPheMetLysHisLeu 100
      —   — — — — — — —           — — — — —         — —   — —
 71 AlaLysGluIleCysAlaAspProLysGln LysTrpValGlnAspSerMetAspHisLeu  90

101 AspLysLysThrGlnThrProLysLeu 109
    — —     — — — — —
 91 AspLysGlnThrGlnThrProLysThr  99
```

```
  1 AGCAGAGGGGCTGAGACCAAACCAGAAACCTCCAATTCTCATGTGGAAGC   50
    ||||||||||||||||| ||||||| |||||||||||||| |||||||||
  1 AACCGAGAGGCTGAGACTAAACCAGACTAAACCAGAAAGATCCAATTCTCAAACTGAAGC   50

51 CCATGCCCTCACCCTCCAACATGAAAGCCTCTGCAGCACTTCTGTCTG  100
    ||||| ||||  |||    |||||||||||||||||||||||||||||
 51 TCGCACTCTC.GCCTCCAGCAGCATGAAAGTCTCTGCCGCCCTTCTGTGCCTG   99

101 CTGCTCACAGCAGCCTGCTTTCAGCCCCCCAGGGGCTGTTGCTCAGCCAGTTGG  150
    |||||||| ||||||||| ||||||  || ||| |||| |||||||||||||
100 CTGCTCATAGCAGCCCACCCTTTCCATTCCCCAAGGGCTCGCTCAGCCAGATGC  149

151 GATTAATACTTCAACTACCTGCTGCTACAGACCTGTTATAACTTCACCAATAGGAAGATCT  200
    |||||||||||| | ||| |||| | |||||  | | || |||||||||||||||||||
150 AATCAATGCCCCAGTCACCTGCTGTTATAACTTCACCAATAGGAAGATCT  199

201 CTAAGCAGAGGCTGGAGAGCTACAGAAGGACCACCAGTAGCCACTGTCCC  250
    |||||||||||||||||||||| ||||| ||||||||| |||||||||
200 CAGTGCAGAGGCTCGCGAGCTATAGAAGACCAGCAGCAAGTGTCCC  249

251 CGGGAAGCTGTAATCTTCAAGACCAATTGGACAAGGAGATCTGTGCTGA  300
    |||||||||||| | ||||||  |||  | |||||||||||||||||
250 AAAGAAGCTGTGATCTTCAAGACCATTGTGGCCAAGGAGATCTGTGCTGA  299

301 CCCCACACAGAAGTGGGTCCAGGACTTTATGAAGCACCTGGACAAGAAAA  350
    ||||   ||||||||||  ||||| |||| ||| |||||||||||||||
300 CCCCAAGCAGAAGTGGGTTCAGGATTCCATGACTGACCACCTGGACAAGCAAA  349

351 CCCAAACTCCAAAGCTTTGAACATTGAACTGACTAAAAACAAGCCAT  400
    |||||||||     |||   |||||||||||| |||||||||||||
350 CCCAAACTCCGAAGACTTGAACACTCACTCC........ACAACCCAA  389
```

FIG. 4b

```
401 GACTTGAGAAACAAATAATTTGTATACCCTGTCCTTTCTCAGAGTGGTTC 450
    ||  |     ||    |||  |||||  |||| ||||  |    |||
390 GAATCTGCAGCTAACTTATTT....TCCCCTAGCTTTCCCAGACACCCTG 436

451 TGAGATTATTTTAATCTAAGGAATATGAGCTTTATGTAATAATG 500
    |  ||||   ||    | ||  || || || ||||| |||||
437 TTTTATTTTATTATAAATGAATTTGTTGTGATGTGAAACATTATGCCT 486

501 TGAATCATGGTTTTTCTTAGTAGATTTTAAAAGTTATTAATTTTAATT 550
    |||| |||||  |     ||   |||   ||||| ||| |||||||
487 TAAGTAATGTTAATTCTTA......TTTAAGTTATTGATGTTTTAAGT 528

551 TAATCTTCCATGGATTTTGGTGGGTTTGAACATAAAGCCTTGGATGTAT 600
          ||  |||       ||||||     |  |||   ||| |||
529 TTATCTTTCATGG.TACTAGTGTTTTTTAGATACAGAGACTTGGGGAAAT 577

601 ATGTCATCTCAGTGCTGTAAAAaCTGTGGGATGCTCCCCTGGGATGTTTTGA 621
    | |||| ||  ||| ||   |  ||   ||||       ||| || ||
578 TGCTTTTC......CTCTTGAACCACAGTTCTACCCCTGGGATGTTTTGA 621

651 TCATGGGgTATTGTATAAGTCCTTGCAaGAatCAGTGCAAAGATNTGCT 700
       |||||  |  |    |  ||||||| || |  ||||  |  |||
622 GGGTCTTTGCA.AGAATCATTAATACAAaGAATTTTTTTAACATTCCAA 670

701 TTAATTGTTAAGATATGATGTCCCTATGGAAGCATATGTTATTATAA 750
    | |||||| ||||   ||  |  ||||| |||  ||   | ||||
671 TGCATTGCTAAAAATATATTGTGGAAATGAA.TATTTTGTAACTATTACA 719

751 TTACATATTTGCATATGTATGACTCCCAAATTTTCACATAAATAGATTT 800
      |||||| | ||| | ||  ||||||||| |||||
720 CCAAATAAATATATTTTTGTAC........................ 741
```

FIG. 5

```
AGCTTGGATAAAGACAGCCAGTTGGGATTAATACTTCAACTACCTGCT
----+----|----+----|----+----|----+----|----+---
          ACCTATTTTCTGTCGGTCAACCCTAATTATGAAGTTGATGGACGA

ACAGATTTATCAATAAGAAAATCCCTAAGCAGAGGCTGGAGAGCTACAGAAGGACCACCA
----+----|----+----|----+----|----+----|----+----|----+----
TGTCTAAATAGTTATTCTTTTAGGGATTCGTCTCCGACCTCTCGATGTCTTCCTGGTGGT

GTAGCCACTGTCCCCGGAAGCTGTAATCTTCAAGACCAAACTGGACAAGGAGATCTGTG
----+----|----+----|----+----|----+----|----+----|----+----
CATCGGTGACAGGGGCCCTTCGACATTAGAAGTTCTGTTTGACCTGTTCCTCTAGACAC

CTGACCCCCACAGAAGTGGGTCCAGGACTTTATGAAGCACCTGACAAGAAACCCAAA
----+----|----+----|----+----|----+----|----+----|----+---
GACTGGGGGTGTGTCTTCACCCAGTCCTGAAATACTTCGTGGACCTGTTCTTTGGGTTT
                                              BamHI

CTCCAAAAACTTTGAG
----+----|------
GAGGTTTTGAAACTCCTAG
```

CHEMOKINE NC28 (MONOCYTE CHEMOTACTIC PROTEIN-3, MCP-3) POLYPEPTIDES AND THEIR RECOMBINANT PRODUCTION

BACKGROUND OF THE INVENTION

The present invention relates to a novel protein having a cytokinin-type activity, to the genetic engineering tools for its production, namely a recombinant DNA, an expression vector carrying this recombinant DNA, and the procaryotic microorganisms and the eucaryotic cells containing this recombinant DNA, and to a drug, useful especially as an anticancer agent or immunomodulator, in which this protein is present as the active principle.

It is well known that the immune system comprises cellular elements and soluble substances, called cytokinins, secreted by said elements. Cytokinins are proteins which effect communication between an emitter cell and a target cell belonging either to the immune system or to another biological system of the organism. In general, cytokinins have a so-called pleiotropic biological activity, i.e. they can have multiple effects on the target cell: proliferation, differentiation, cytolysis, activation, chemotaxis etc. Several of these molecules have already found applications in therapeutics: for example, interleukin-2 or interferon-α used for the treatment of certain tumors by immuno-therapy, and myelopoietic factors, such as GCSF (Granulocyte Colony Stimulating Factor) or GMCSF (Granulocyte Monocyte Colony Stimulating Factor), which stimulate the growth and differentiation of blood cells and whereby blood which has been impoverished in blood cells as a result of chemotherapy can be enriched therewith.

One of the first cytokinins to be discovered was interleukin-1, to which a central activity in inflammation—chemotaxis of neutrophils—was initially attributed following experiments showing an activity of this type in vivo after injection (J. Oppenheim et al., 1986, Imm. Today, 7, 45–56). It is now known that interleukin-1 stimulates in vivo the expression of another cytokinin which is chemotactic towards neutrophils, namely interleukin-8 (originally called Neutrophil Chemotactic Factor, NCF). This cytokinin, whose amino acid sequence was determined in 1987 after isolation and purification and also by cloning and sequencing of its complementary DNA (K. Matsushima et al., 1988, J. Exp. Med., 1883–1893), is homologous with other cytokinins already known at the time of its discovery, namely the cytokinins produced by the α granules of platelets, such as PF4 (Platelet Factor 4) and PBP (Platelet Basic Protein). The family of known proteins homologous with interleukin-8, usually called the SIS family (representing Small Induced Secreted proteins), has grown considerably since 1987 [J. Oppenheim et al., 1991, Ann. Rev. Immun., 9, 617]. It currently includes the following cytokinins in particular: gro (also called MGSA: Melanoma Growth Stimulatory Activity) described by A. Anisowicz et al., 1987, Proc. Ntl. Acad. Sci. U.S.A., 84, 7188–7192, and A. Richmond et al., 1988, EMBO J., 7, 2025–2033, RANTES (Regulated upon Activation Normal T Expressed and presumably Secreted) described by T. Schall et al., 1988, J. Imm., 141, 1018–1025, MIP-1 (Macrophage Inflammatory Protein 1) described by S. D. Wolpe et al., 1988, J. Exp. Med., 167, 570–581, MIP-2 (Macrophage Inflammatory Protein 2) described by S. D. Wolpe et al., 1989, Proc. Ntl. Acad. Sci. U.S.A., 86, 612–616, and MCP-1 (Monocyte Chemoattractant Protein 1, also called MCAF: Monocyte Chemotactic and Activating Factor) described by Yoshimura et al., 1989, Proc. Ntl. Acad. Sci. U.S.A., 84, 9233–9237, and K. Matsushima et al., 1989, J. Expr. Med., 169, 1485–1489.

The cytokinin MCP-1, isolated from a line of gliomas by T. Yoshimura, op. cit., and from a line of monocytes by K. Matsushima et al., op. cit., exists in two forms with apparent molecular weights of 13 and 15 kDa, called MCP-1α and MCP-1β, which seem to correspond to post-translational modifications [Y. Jiang et al., 1990, J. Biol. Chem., 265, 1318–321]. The cytokinin MCP-1 has a chemotactic activity towards monocytes and basophils but not towards neutrophils (E. J. Leonard, 1990, Immunology Today, 11, 3, 97–101) and a stimulating effect on the cytostatic activity of monocytes on certain tumoral lines (K. Matsushima et al., 1989, J. Exp. Med., 169, 1485–1490).

Three-dimensional structural studies on interleukin-8 and PF4 by nuclear magnetic resonance spectroscopy or X-ray diffraction have shown that these two cytokinins have the same conformation, with a carboxy-terminal peptide of 12 to 15 amino acids in the form of an α helix (R. St. Charles et al., 1988, J. Biol. Chem., 264, 4, 2092–2099, and G. M. Clore, 1990, Biochem., 29, 1689–1696). According to G. M. Clore, the majority of cytokinins in the SIS family have such a carboxy-terminal part in the form of an a helix, the role of this helix being as yet undetermined [C. Herbert et al., 1991, J. Biol. Chem., 266, 18989–994].

It has recently been shown that the carboxy-terminal peptide of 13 amino acids can have the anti-angiogenic activity (inhibition of the proliferation of blood vessels) of the cytokinin PF4 (T. Maione et al., 1990, Science, 247, 77–79). According to D. G. Osterman, 1982, Biochem. Biophys. Res. Commun., 107, 130–135, this peptide has a chemotactic activity towards monocytes which is thirty times greater than that of PF4.

SUMMARY OF THE INVENTION

The present invention relates to a novel protein having a cytokinin-type activity, which comprises the following sequence (a1) (SEQ ID NO:1):

```
Met Lys His Leu Asp Lys Lys Thr Gln Thr Pro Lys Leu
1               5                   10
``` and, immediately upstream of the sequence (a1), a part of the following sequence (a2) (SEQ ID NO:2):

```
Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20              25                  30

Ser Ser His Cys Pro Arg Glu Ala Val Ile Phe Lys Thr Lys Leu Asp
            35              40                  45

Lys Glu Ile Cys Ala Asp Pro Thr Gln Lys Trp Val Gln Asp Phe
    50              55                  60
``` or a sequence which differs from said sequence (a2) by one or more amino acids and gives the protein the same activity, or which comprises the sequence (a2 (SEQ ID NO:2)):

```
Gln Pro Val Gly Ile Asn Thr Ser Thr Thr Cys Cys Tyr Arg Phe Ile
 1           5                   10                      15

Asn Lys Lys Ile Pro Lys Gln Arg Leu Glu Ser Tyr Arg Arg Thr Thr
             20              25                  30

Ser Ser His Cys Pro Arg Glu Ala Val Ile Phe Lys Thr Lys Leu Asp
         35              40                  45

Lys Glu Ile Cys Ala Asp Pro Thr Gln Lys Trp Val Gln Asp Phe
 50                  55                  60
``` and, immediately downstream of (a2), the sequence (a1) (SEQ ID NO:1):

```
Met Lys His Leu Asp Lys Lys Thr Gln Thr Pro Lys Leu
 1           5                   10
``` or a sequence which differs from the sequence (a1) by one or more amino acids and gives the protein the same activity.

The part of the sequence (a2) immediately upstream of the sequence (a1) can be selected from the following sequences:

```
Gln Lys Trp Val Gln Asp     (amino acids 57–63 of SEQ ID NO:2)     Phe et Gln Asp Phe
 1           5
```

Preferably, the part of the sequence (a2) immediately upstream of the sequence (a1) is selected from the sequence (a2) and the following sequences (a3) (SEQ ID NO:3) and (a4):

```
(a3) Val Gly Ile Asn Thr Ser Thr Thr Cys Cys Tyr Arg Phe Ile Asn Lys
      1               5                  10                      15

Lys Ile Pro Lys Gln Arg Leu Glu Ser Tyr Arg Arg Thr Thr Ser Ser
                  20              25                  30

His Cys Pro Arg Glu Ala Val Ile Phe Lys Thr Lys Leu Asp Lys Glu
              35                  40                  45

Ile Cys Ala Asp Pro Thr Gln Lys Trp Val Gln Asp Phe
      50                  55                  60
``` and

```
(a4) (SEQ ID NOs. 2–4, respectively      Lys Ile Pro Lys Gln Arg Leu Glu Ser Tyr Arg Arg Thr Thr Ser Ser
                                          1               5                  10                      15

His Cys Pro Arg Glu Ala Val Ile Phe Lys Thr Lys Leu Asp Lys Glu
                                                      20                  25                  30

Ile Cys Ala Asp Pro Thr Gln Lys Trp Val Gln Asp Phe
                                                  35                  40                  45
``` or from the sequences which differ from the sequence (a2), (a3) or (a4) by one or more amino acids and give the protein the same activity.

The sequence (a2) (SEQ ID NO:2) is particularly valued, the protein possibly having amino-terminal blocking in this case. The sequence of the protein and the amino-terminal blocking probably correspond to those of the protein exported from peripheral blood mononuclear cells under conditions stimulating the expression of cytokinins. As far as their amino acid sequences are concerned, this protein bears a certain resemblance to the cytokinin MCP-1 and, like the latter, possesses a cytokinin-type activity. It constitutes a new member of the SIS family.

This protein is preferably in a form which has an apparent molecular weight, determined by polyacrylamide gel electrophoresis in the presence of SDS, of 9±2, 11±2 or 16±2 kDa. This protein is advantageously N-glycosylated particularly when it is in a form with an apparent molecular weight of 16±2 kDa. This protein is advantageously O-glycosylated particularly when it is in a form with an apparent molecular weight of 11±2 kDa.

This protein preferably has a degree of purity, determined by polyacrylamide gel electrophoresis in the presence of SDS and developing with silver nitrate, of more than 90% and in particular of more than 95%.

The invention further relates to a recombinant DNA which codes for the above protein, the latter then being obtainable from the cell lysate, or, advantageously, for a precursor of the above protein. This precursor preferably comprises a signal sequence.

The function of this signal sequence, which is chosen according to the host cell, is to make it possible for the recombinant protein to be exported out of the cytoplasm, which enables the recombinant protein to adopt a conformation similar to that of the natural protein and considerably facilitates its purification. This signal sequence can be cleaved either in a single step by a signal peptidase released by the mature protein, or in several steps if this signal sequence comprises, in addition to the sequence removed by the signal peptidase, called a signal peptide or pre-sequence, a sequence which is removed at a later stage during one or more proteolytic events, called a pro-sequence.

For expression in procaryotic microorganisms such as, for example, *Escherichia coli*, this signal sequence can be either a sequence derived from a natural precursor of a protein exported by a procaryotic microorganism (for example the signal peptide OMPa (Grayeb et al., 1984, EMBO Journal, 3, 2437–2442) or that of alkaline phosphatase (Michaelis et al., J. Bact., 1983, 154, 366–374)), or a non-endogenous sequence originating from a eucaryotic precursor (for example the signal peptide of one of the natural precursors of human growth hormone), or a synthetic signal peptide (for example the one described in French patent application no. 2 636 643, of the sequence (SEQ ID NO:5)

For expression in animal cells, the signal sequence used is either a signal sequence of an animal cell protein known to be exported—for example the signal peptide of one of the natural precursors of human growth hormone, which is already known for permitting the secretion of interleukin-2 (cf. French patent application no. 2 619 711)—or one of the three signal sequences described below.

```
Met Ala Pro Ser Gly Lys Ser- Thr Leu Leu Leu Phe Leu Leu Leu
 1           5                10                  15

Cys Leu Pro Ser Trp Asn Ala Gly Ala).
             20              25
```

For expression in eucaryotic cells such as Ascomycetes, for example the yeast *Saccharomyces cerevisiae* or the filamentous fungus *Crythonectria parasitica*, this signal sequence is preferably a sequence derived from a natural precursor of a protein secreted by these cells, for example, for the yeast, the natural precursor of invertase (European patent application 0123289) or the precursor of the prepro-sequence of pheromone alpha (Danish patent application 2484/84) or, for *Cryphonectria parasitica*, that of the prepro-sequence of endothiapepsin, of the sequence (SEQ ID NO:6)

```
Met Ser Ser Pro Leu Lys Asn-Ala Leu Val Thr Ala Met Leu Ala Gly
 1           5                10                  15

Gly Ala Leu Ser Ser Pro Thr Lys Gln His Val Gly Ile Pro Val Asn
             20              25                  30

Ala Ser Pro Glu Val Gly Pro Gly Lys Tyr Ser Phe Lys Gln Val Arg
         35              40                  45

Asn Pro Asn Tyr Lys Phe Asn Gly Pro Leu Ser Val Lys Lys Thr Tyr
     50              55              60

Leu Lys Tyr Gly Val Pro Ile Pro Ala Trp Leu Glu Asp Ala Val Gln
 65              70              75                  80

Asn Ser Thr Ser Gly Leu Ala Glu Arg
                 85
```

```
(b1) (SEQ ID NO:7)   Met Lys Ala Ser Ala Ala Leu Leu Cys Leu Leu Leu Thr Ala Ala Ala
                      1               5                10                15

Phe Ser Pro Gln Gly Leu Ala
                                     20

(b2) (SEQ ID NO:8)   Met Pro Ser Pro Ser Asn Met Lys Ala Ser Ala Ala Leu Leu Cys Leu
                      1               5                10                15

Leu Leu Thr Ala Ala Ala Phe Ser Pro Gln Gly Leu Ala
                                 20                  25 and (b3) (SEQ ID NO:9)   Met Trp Lys Pro Met Pro Ser Pro Ser Asn Met Lys Ala Ser Ala Ala
                      1               5                10                15

Leu Leu Cys Leu Leu Leu Thr Ala Ala Ala Phe Ser Pro Gln Gly Leu
                                     20              25                  30

Ala
``` advantageously coded by the following sequences (Nb1) (SEQ ID NO:10), (Nb2) (SEQ ID NO:11) and (Nb3):

(Nb1) ATGAAAGCCT CTGCAGCACT TCTGTGTCTG CTGCTCACAG CAGCTGCJT CAGCCCCCAG GGGCTTGCT (Nb2) ATGCCCTCAC CCTCCAACAT GAAAGCCTCT GCAGCACTTC TGTGTCTGCT GCTCACAGCA GCTGCTTCA GCCCCCAGGG GCrTGCT and (Nb3) (SEQ ID NO:12) ATGTGGAAGC CCATGC- CCTC ACCCFCCAAC ATGAAAGCCT CTGCAG- CACT TCTGTGTCTG CTGCFCACAG CAGCT- GCJTT CAGCCCCCAG GGGCTTGCT The nucleotide sequence coding for the mature protein is for example the following sequence (Na2) (SEQ ID NO:13):

CAGCCAGTTG GGATTAATAC TTCAACTACC TGCTGCTACA GATTTATCAA TAAGAAAATC CCTAAGCAGA GGCTGGAGAG CTACAGAAGG ACCACCAGTA GCCACTGTCC CCGGGAAGCT GTAATCTTCA AGACCAAACT GGACAAGGAG ATCTGTGCTG ACCCCACACA GAAGTGGGTC CAGGACTTA TGAAGCACCT GGACAAGAAA ACCCAAACTC CAAAGCTT

The invention further relates to an expression vector which carries the above-defined recombinant DNA together with the means necessary for its expression.

For expression in procaryotic microorganisms, in particular in *Escherichia coli*, the recombinant DNA has to be inserted into an expression vector containing especially an effective promoter, followed by a ribosome binding site upstream of the gene to be expressed, and an effective transcription termination sequence downstream of the gene to be expressed. This vector also has to contain an origin of replication and a selection marker. All these sequences have to be chosen according to the host cell.

For expression in eucaryotic cells, the expression vector according to the invention carries the above-defined recombinant DNA together with the means necessary for its expression and, if appropriate, the means necessary for its replication in eucaryotic cells, and/or for selection of the transformed cells. Preferably, this vector carries a selection marker, chosen for example so as to complement a mutation of the recipient eucaryotic cells, which permits selection of the cells which have integrated the recombinant DNA in a large number of copies, either into their genome or into a multicopy vector.

For expression in eucaryotic cells such as yeast, for example *Saccharomyces cerevisiae*, it is necessary to insert the recombinant DNA between sequences recognized as an effective promoter, on the one hand, and a transcription terminator, on the other. The promoter/coding sequence/ terminator assembly, called an expression cassette, is either cloned in a single-copy or multicopy plasmid vector for the yeast, or integrated in multicopy into the genome of the yeast.

The invention further relates to the yeast which contains the above-defined recombinant DNA together with the means necessary for its expression.

The invention further relates to a method of preparing the above protein, which comprises a step for the culture of this yeast, followed by the isolation and purification of the recombinant protein.

For expression in eucaryotic cells such as those of filamentous fungi of the Ascomycetes group, for example the fungi of the genera Aspergillus, Neurospora, Podospora, Trichoderma or Cryphonectria, the expression vector according to the invention carries the above-defined recombinant DNA together with the means necessary for its expression, and, if appropriate, a selection marker and/or telomeric sequences. It is in fact possible to select the transformants which have integrated a DNA of interest with the aid of a selection marker located either on the same vector as the DNA of interest or on another vector, these two vectors then being introduced by cotransformation. The recombinant DNA of the invention can be either integrated into the genome of the filamentous fungi or conserved in extrachromosomal form by virtue of sequences permitting the replication and partition of this DNA.

For expression in animal cells, especially in the cells of Chinese hamster ovaries, CHO, the recombinant DNA is preferably inserted into a plasmid (for example derived from pBR322) containing either a single expression unit into which the recombinant DNA of the invention is inserted, and, if appropriate, a selection marker, in front of an effective promoter, or two expression units. The first expression unit contains the above recombinant DNA preceded by an effective promoter (for example SV40 early promoter). The sequence around the initiation ATG is preferably chosen according to the consensus sequence described by KOZAK (M. KOZAK (1978) Cell, 15, 1109–1123). An intron sequence, for example a sequence of the intron of mouse α-globin, can be inserted upstream of the recombinant DNA, and a sequence containing a polyadenylation site, for example an SV40 polyadenylation sequence, can be inserted downstream of the recombinant gene. The second expression unit contains a selection marker, for example a DNA sequence coding for dihydrofolate reductase (an enzyme abbreviated hereafter to DHFR). The plasmid is transfected into the animal cells, for example the CHO dhfr-cells (incapable of expressing DHFR). A line is selected for its methotrexate resistance: it has integrated a large number of copies of the recombinant DNA into its genome and expresses said DNA at a sufficient level.

The invention further relates to the animal cells which contain this recombinant DNA together with the means necessary for its expression. Said DNA may, for example, have been introduced into the cells by transfection by the above expression vector, by infection by means of a virus or a retrovirus carrying said DNA, or by microinjection. Preferred animal cells are CHO cells, in particular CHO dhfr-cells, from which it is possible to obtain lines which are highly productive in terms of the protein of the invention. COS cells also constitute an advantageous host for obtaining this protein.

The invention further relates to a method of preparing the above-defined protein, which comprises a step for the culture of the above animal cells, followed by the isolation and purification of the recombinant protein.

The invention further relates to the recombinant protein obtainable by a method which comprises a step for the culture of these animal cells, followed by the isolation and purification of the recombinant protein.

The protein of the invention is a cytokinin possessing a chemotactic activity towards monocytes, i.e. cells capable of inhibiting tumor growth (B. J. Rollins et al., 1991, Molecular and Cellular Biology, 11, 6, 3125–3131) and of eliminating certain parasites such as *Leishmania major* (S. Stenger et al., 1991, Eur. J. Immunol., 21, 327–33).

The invention therefore further relates to the drug which is useful especially in oncology and in the treatment of certain infectious conditions during which the immune defenses are weakened, for example due to the presence of certain parasites (for example leishmaniasis, leprosy or Chagas' disease), in which drug the above-defined protein or peptide is present as the active principle in a pharmaceutically acceptable excipient. Said active principles can be used by themselves or in association with other active agents, for example one or more other cytokinins.

The invention will be understood more clearly with the aid of the following description, divided up into sections, which comprises experimental results and a discussion thereof. Some of these sections concern experiments performed with the aim of putting the invention into effect, and others concern practical Examples of the invention, which of course are given purely by way of illustration.

The techniques below, which are well known to those skilled in the art, are all largely explained in detail in the work by Sambrook et al.: "Molecular Cloning: A Laboratory Manual" published in 1989 by Cold Spring Harbor Press in New York (2nd edition).

BRIEF DESCRIPTION OF THE DRAWINGS

The following description will be understood more clearly with the aid of FIGS. 1a, 1b, 2 to 5, 6a, 6b and 6c.

FIG. 1b shows the sequence (SEQ ID NO:14) of the synthetic "site binding to HindIII"—HindIII fragment used in the assembly of plasmid pSE1.

FIG. 2 shows the nucleotide sequence of NC28 cDNA (SEQ ID NO:15) and, underneath, the translated amino acid sequence, (SEQ ID NO:16) the three Met capable of initiating translation being underlined, the probable cleavage site of the signal peptide being indicated by a vertical arrow and the potential N-glycosylation site being underlined with a broken line.

FIG. 3 (SEQ ID NOS.16 and 24) and FIG. 4 (bases 1–800 of SEQ ID NO:15 and SEQ ID NO:25) respectively show the maximum homology alignment, according to the method of Needleman and Wunsch, 1970, J. Mol. Biol., 48, 443–453, of the amino acid sequence translated from NC28 cDNA (upper line, (SEQ ID NO:16)) and of the amino acid sequence translated from the cDNA of the cytokinin MCP-1 (lower line (SEQ ID NO:24)), and the alignment, according to this method, of NC28 cDNA (upper line, bases 1–800 of SEQ ID NO:15) and of the cDNA of the cytokinin MCP-1 (lower line SEQ ID NO:25).

FIG. 5 shows the sequence (SEQ ID NO:17) of the fragment B used in the construction of plasmid pEMR617, a vector for expression in yeast.

FIG. 6a shows the number of cells per microscopic field as a function of the concentration expressed in nM for purified protein NC28 derived from yeast, purified protein NC28 derived from COS cells and peptides C13, C16, C20 and fMLP.

FIG. 6b shows the number of cells per microscopic field as a function of the concentration expressed in ng/ml for purified protein NC28 derived from yeast and purified cytokinin MCP-1 derived from COS cells.

FIG. 6c shows the number of cells per microscopic field as a function of the concentration expressed in ng/ml for purified protein NC28 derived from yeast, cytokinin IL-8 and peptide fMLP.

DETAILED DESCRIPTION OF THE INVENTION

SECTION 1

Figure 1A:
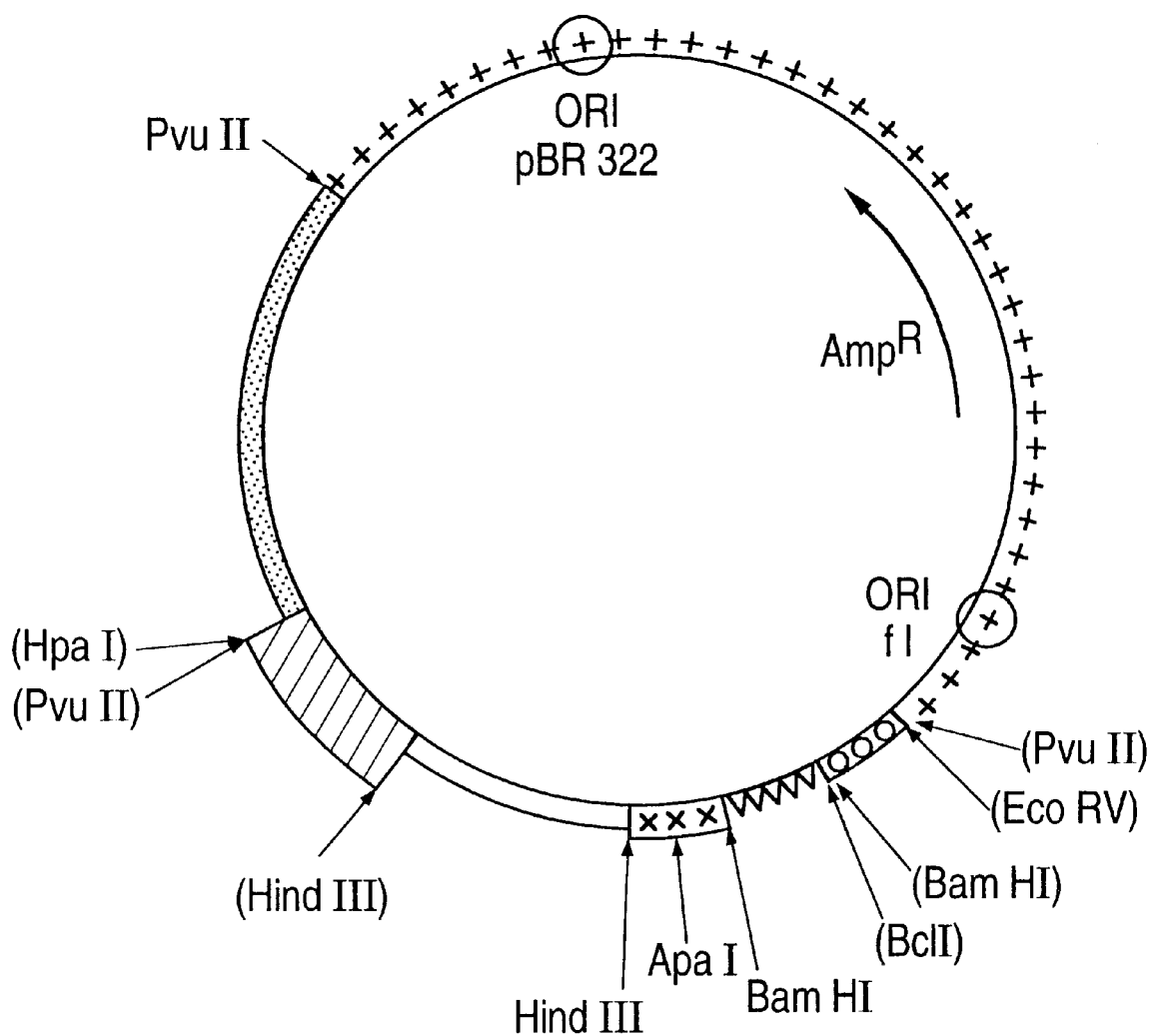
FIG. 1a shows an assembly map of plasmid pSE1, a plasmid for cloning in E. coli and for expression in animal cells, the sites which have disappeared through ligation being indicated in brackets. The symbols used in this Figure will be explained in the description of this plasmid (section 2).

Culture and Stimulation of Peripheral Blood Mononuclear Cells with the Aid of PMA and PHA-P—Preparation of the Messenger RNA Used to Prepare the Complementary DNA Library 1) Culture and Stimulation of Peripheral Blood Mononuclear Cells A cell fraction enriched in peripheral blood mononuclear cells, PBMNC, of the following approximate composition: 70% of lymphocytes, 25% of monocytes and 5% of granulocytes (cells counted using a COULTER MODEL S. PLUS IV cell counter), is taken from bags of peripheral blood (obtained from three healthy volunteers in a blood transfusion center) which has first undergone cytapheresis and a FICOLL® gradient (Gauchat et al., 1989, Eur. J. Imm., 19, 1079).

The cells are collected in a 250 ml flask and then centrifuged for 10 min at 37° C. The supernatant is removed and the cell residue is rinsed with 50 ml of a medium based on glucose, mineral salts, amino acids and vitamins, called RPMI medium (RPMI 1640 medium from Gibco BRL), and then centrifuged again under the same conditions.

The cell residue is then taken up with 500 ml of RPMI medium complemented with 10% of fetal calf serum (Gibco BRL—ref. 013-06290H), to which 10 units of penicillin and 10 μg of streptomycin (solution of penicillin/streptomycin from Gibco, ref. 043-05140D) have been added per ml of medium and to which L-glutamine (Gibco BRL—ref. 043-05030D) has been added to a final concentration of 2 mM.

Part of the cell suspension is divided up for separation of the adhesive cells and the non-adhesive cells, at a rate of about 100 ml per dish, in four large square culture dishes (245×245×20 mm—Nunc—ref. 166508), and incubated for 1 h at 37° C. It is in fact known that the majority of monocytes adhere to the culture dish, whereas the majority of lymphocytes remain in suspension.

The non-adhesive cells are sucked off with a pipette and cultivated in Falcon-type culture flasks with a surface area of 175 $cm^2$, in the presence of RPMI medium complemented as described above, to which 10 ng/ml of phorbol 2-myristate-3-acetate (PMA) (Sigma—ref. P8139) and 5 μg/ml of phytohemagglutinin (PHA-P) (Sigma—ref. L8754) have been added, at 37° C, in the presence of 5% of $CO_2$, for 24 h. 100 ml of RPMI medium complemented as described above, to which 10 ng/ml of PMA and 5 pg/ml of PHA-P have been added, are added to the adhesive cells. The cells are incubated at 37° C., in the presence of 5% (v/v) of $CO_2$, for 5 h.

The remainder of the cell suspension, hereafter called the whole cells, is divided up into 4 large square culture dishes and incubated in the presence of RPMI medium complemented as described above, to which 10 ng/ml of PMA and 5 μg/ml of PHA-P have been added, at 37° C., in the presence of 5% (v/v) of $CO_2$, for 5 h in the case of the first two dishes and 24 h in the case of the other two.

About 2 h before incubation ends, 10 μg/ml of cycloheximide (Sigma—ref. C6255) (a translation inhibitor which increases the stability of the RNAs of the cytokinins: cf. T. Lindsten et al., 1989, Science, 244, 339–344) are added to the culture medium of these different cells and incubation is continued for 2 h at 37° C.

2) Preparation of the Messenger RNA a) Extraction of the Messenger RNA

The cells are recovered in the following manner:

The adhesive cells are washed twice with PBS (Phosphate Buffered Saline, ref. 04104040—Gibco BRL) and then scraped with a rubber scraper and centrifuged. This gives a cell residue called residue A.

For the non-adhesive cells, after the flask containing the cell suspension has been shaken, the cell suspension is removed and centrifuged. This gives a cell residue called cell residue NA.

For the whole cells, the adhesive fraction is washed twice with PBS, scraped as above and then centrifuged. The non-adhesive fraction is centrifuged. The two cell residues obtained will subsequently be combined. This combination is called cell residue T(5 h) in the case of the whole cells incubated for 5 h, and T(24 h) in the case of the whole cells incubated for 24 h.

The cell residues A, NA, T(5 h) and T(24 h) are frozen and kept at −80° C.

Each frozen cell residue is suspended in a lysis buffer of the following composition: guanidine thiocyanate 5 M, tris(hydroxymethyl)aminomethane 50 mM pH 7.5 and EDTA 10 mM. The suspension is sonicated using an ULTRA TURRAX® no. 231 256 sonicator (Janke and Kunkel) at maximum power for four 20 s cycles. β-Mercaptoethanol is added to 0.2 M and a 30 s sonication cycle is carried out. Lithium chloride is added to 3 M. The suspension is cooled to 4° C. and left to stand at this temperature for 48 h. The RNA is then isolated by centrifugation for 60 min. The RNA residue is washed once with a 3 M solution of lithium chloride, centrifuged again and then taken up in a buffer of the following composition: SDS 1%, EDTA 5 mM and Tris-HCl 10 mM pH 7.5, to which 1 mg/ml of proteinase K (Boehringer Mannheim, GmbH) has been added. After incubation at 40° C. for 1 h, the RNA solution is extracted with a phenol/chloroform mixture. The RNA contained in the aqueous phase is precipitated at −20° C. with a solution of ammonium acetate of final concentration 0.3 M and 2.5 volumes of ethanol. The mixture is centrifuged at 15,000 g for 30 min and the residue is retained.

b) Purification of the Poly A⁺ Fraction of the RNA

The residue is taken up in 1 ml of a buffer of the following composition: Tris-HCl 10 mM pH 7.5 and EDTA 1 mM, called TE buffer, and suspended by agitation on a Vortex. Type 3 oligo dT-cellulose (marketed by Collaborative Research Inc., Biomedicals Product Division) is prepared according to the manufacturer's recommendations. The RNA is deposited on the oligo dT-cellulose, shaken gently to suspend the beads and then heated for 1 min at 65° C.

The suspension is adjusted to 0.5 M with NaCl and then shaken gently for 10 min. The suspension is then centrifuged for 1 min at 1000 g, the supernatant is removed and the residue is washed twice with 1 ml of TE buffer containing 0.5 M NaCl. The supernatants are removed. The polyadenylated fraction of the RNAs (consisting of the messenger RNAS) is eluted by suspending the beads in 1 ml of TE buffer, then heating this suspension at 60° C. for 1 min and then shaking for 10 min on a tilting plate. The suspension is then centrifuged for 1 min at 1000 g, making it possible to recover the supernatant containing free messenger RNAs in solution. The above series of operations (as from elution) is repeated twice. The supernatants thus obtained are pooled, the residual beads are removed by centrifiguation and the supernatant is precipitated with 3 volumes of ethanol and a solution of NaCl of final concentration 0.3 M.

Starting from the cell residues A, NA, T(5 h) and T(24 h), this procedure gives four samples of RNA-poly A⁺, hereafter referred to as RNA-poly A⁺-A, RNA-poly A⁺-NA, RNA-poly A⁺-T(5 h) and RNA-poly A⁺-T(24 h).

SECTION 2

Preparation of a Complementary DNA Library Enriched in Sequences Specific for Peripheral Blood Mononuclear Cells 1) Construction of Cloning Vector pSE1

The strategy employed uses fragments obtained from pre-existing plasmids available to the public, and fragments synthesized by the techniques now in common use. The cloning techniques employed are those described by T. Maniatis, E. F. Fritsch and J. Sambrook in "Molecular Cloning, A Laboratory Manual" (Cold Spring Harbor Laboratory, 1984). The oligonucleotides are synthesized using a BIOSEARCH 8700 DNA synthesizer.

The following description will be understood more clearly with reference to FIG. 1a.

This plasmid was constructed by successive ligation of the following elements:

a)—a PvuII—PvuII fragment—symbolized by +++++++ in FIG. 1a—of 2525 bp, obtained by complete digestion of plasmid pTZ18R (Pharmacia) with the restriction enzyme PvuII. This fragment contains the origin of replication of phage f1 (indicated as ORI F1 in FIG. 1a), a gene (indicated as Amp^R in FIG. 1a) carrying ampicillin resistance and the origin of replication (indicated as ORI pBR322 in FIG. 1a) permitting the replication of this plasmid in E. coli. The first PvuII blunt site disappears through ligation with the EcoRV blunt site (which also disappears) of the fragment described in g).

b)—a PvuII-HpaI fragment—symbolized by ▬▬▬ in FIG. 1a—of 1060 bp, of type 5 adenovirus DNA between position 11299 (PvuII restriction site) and position 10239 (HpaI restriction site) (Dekker and Van Ormondt, Gene, 27, 1984, 115–120) containing the information for the RNAs VA-I and VA-II. The HpaI blunt site disappears through ligation with the PvuII blunt site (which also disappears) of the fragment described in c). The ApaI site in position 11218 was removed by cleavage with the enzyme ApaI, exonucleolytic treatment with the DNA polymerase of phage T4 and religation.

c)—a PvuII-HindIII fragment—symbolized by ▰▰▰ in FIG. 1a—of 344 bp, derived from SV40 DNA obtained by complete digestion with the restriction enzymes PvuII and HindIII. This fragment contains the origin of replication and the early promoter of SV40 DNA (ref. B. J. Byrne et al., Proc. Ntl. Acad. Sci. U.S.A. (1983) 80, 721–725).

The HindIII site disappears through ligation with the site binding to HindIII of the fragment described in d).

d)—a synthetic "site binding to HindIII"—HindIII fragment—symbolized by ═══ in FIG. 1a—of 419 bp, whose sequence, given in FIG. 1b, contains a sequence similar to the untranslated 5' sequence of HTLV1 (R. WEISS et al., "Molecular Biology of Tumor Viruses"—part 2—2nd edition—1985—Cold Spring Harbor Laboratory—p. 1057) and the distal intron of the mouse α-globin gene (Y. Nishioka et al., 1979, Cell, 18, 875–882).

e)—a synthetic HindIII—"site binding to BamHII" fragment—symbolized by XXXXXXX in FIG. 1a—containing the promoter of the RNA polymerase of phage T7 as well as a polylinker containing especially the ApaI and BamHI cloning sites(SEQ ID NO:18):

AGCTTGTCGACTAATACGACTCACTATAGGGCGGCCGCGGGCCCT

-continued

```
ACAGCTGATTATGCTGAGTGATATCCCGCCGGCGCCCGGGGA
▲
  HindIII  BamHI          site binding to BamHI
          ▼                       ▼
GCAGGAATTCGGATCCCCCGGGTGACTGACT

CGTCCTTAAGCCTAGGGGGCCCACTGACTGACTAG
``` f)—a BamHI-BclI fragment—symbolized by ▲▲▲▲▲▲▲▲ in FIG. 1a—of 240 bp, this being the small fragment obtained by complete digestion of SV40 DNA with the enzymes BclI and BamHI and containing the SV40 late polyadenylation site (M. Fitzgerald et al., Cell, 24, 1981, 251–260). The BamHI and BclI sites disappear through ligation respectively with the "site binding to BamHI" of the fragment described in e) and the BamHI site (which also disappears) of the fragment described in g).

g)—a BamHI-EcoRV fragment—symbolized by OOOOOO in FIG. 1a—of 190 bp, this being the small fragment derived from plasmid pBR322 after complete digestion with the enzymes EcoRV and BamHI.

Plasmid pSE1 therefore contains the elements necessary for its use as a cloning vector in *E. coli* (origin of replication in *E. coli* and ampicillin resistance gene, originating from plasmid pTZ18R) and as an expression vector in animal cells (promoter, intron, polyadenylation site, origin of replication of SV40), and for its single-stranded copy with a view to sequencing (origin of replication of phage f1).

2) Constitution of a Complementary DNA Library Enriched in Sequences Specific for Peripheral Blood Mononuclear Cells The cloning technique used is the one described by Caput et al. (primer-adapter technique: Caput et al., Proc. Natl. Acad. Sci. (U.S.A.), 1986, 83, 1670–1674).

It consists on the one hand in digesting vector pSE1 with ApaI, adding a polydC tail to the protuberant 3' end and then digesting the resulting plasmids with the endonuclease BamHI. The fragment corresponding to the vector is purified on a column of SEPHAROSE® CL4B (Pharmacia). It therefore comprises a polydC tail at one end, the other end being a sticky end of the BamHI type.

On the other hand, the RNA-poly A+s obtained at the end of section 1 are subjected to reverse transcription starting from a primer having the following sequence (SEQ ID NO:19):

5' GATCCGGGCCCTTTTTTTTTTTT 3'

Thus, at their 5' end, the cDNAs have the sequence GATCC complementary to the BamHI sticky end.

The RNA-DNA hybrids obtained by the action of reverse transcriptase are subjected to alkaline hydrolysis, which makes it possible to remove the RNA. The single-stranded cDNAs are then subjected to a treatment with terminal transferase so as to add polydGs at the 3' end, and purified by 2 cycles on a column of SEPHAROSE® CL4B.

These cDNAs are hybridized with RNA-poly A+ originating from cells of the COS3 line (monkey kidney cell line expressing SV40 T-antigen: cf. Y. Gluzman, 1981, Cell, 23, 175–182, prepared as described in section 1.2).

The unhybridized cDNAs are isolated (fraction enriched in DNA complementary to the messenger RNAs specific for peripheral blood mononuclear cells).

These cDNAs are inserted in single-stranded form into vector pSE1. A second oligonucleotide (the adapter), complementary to the primer, is necessary for generating a BamHI site at the 5' end of the cDNAs. After hybridization of the vector, the cDNA and the adapter, the recombinant molecules are annealed by the action of the ligase of phage T4. The single-stranded regions are then repaired by the DNA polymerase of phage T4. The resulting pool of plasmids is used to transform the strain *E. coli* MC1061 (Casabadan and S. Cohen, J. Bact. (1980) 143, 971–980) by electroporation.

Protocol for Preparation of the Complementary DNA Library a) Preparation of the Complementary DNA Starting from 5 µg of the RNA-poly A+s of peripheral blood mononuclear cells obtained at the end of section 1, of the following composition: RNA-poly A+-A: 0.5 µg, RNA-poly A+-NA: 2 µg, RNA-poly A+-T(5 h): 2 µg and RNA-poly A+-T(24 h): 0.5 µg, the single-stranded complementary DNA labeled with $^{32}$P-dCTP (the complementary DNA obtained has a specific activity of 3000 dpm/ng) is prepared with the synthetic primer of the following sequence (SEQ ID NO:19) (comprising a BamHI site):

5' GATCCGGGCCCTTTTTTTTTTTT 3' in a volume of 100 µl. After incubation for 30 min at 46° C. with 100 units of the enzyme reverse transcriptase (Genofit—E1 022), 4 µl of EDTA 0.5 M are added. A first extraction is carried out with phenol (saturated with TE buffer) and then a second with chloroform. The following are added: 10 µg of calf liver transfer RNA, and 1/10 volume of a 10 M solution of ammonium acetate and 2.5 volumes of ethanol to precipitate the complementary DNA. The mixture is centrifuged, the residue is dissolved in 30 µl of TE buffer and the small molecules such as salts, phenol and chloroform are then removed by exclusion chromatography on a column of polyacrylamide P10 (Biogel P10-200-400 mesh, ref. 1501050—Biorad).

b) Alkaline Hydrolysis of the RNA Template 4.6 µl of a 2 N solution of NaOH are added, incubation is carried out for 30 min at 68° C., 4.6 µl of 2 N acetic acid are then added and the solution obtained is passed over a column of polyacrylamide P10.

c) Homopolymeric Addition of dG

The complementary DNA is extended at the 3' end with a dG "tail" using 66 units of the enzyme terminal transferase (Pharmacia—27073001). Incubation is carried out for 30 min at 37° C. and 4 µl of EDTA 0.5 M are then added.

d) Purification on a Column of SEPHAROSE® CL4B

To remove the synthetic primer, the complementary DNA is purified on two successive columns of 1 ml of SEPHAROSE® CL4B (Pharmacia) equilibrated with a solution of NaOH 30 mM/EDTA 2 mM.

The first three radioactive fractions (of about 80 µl each) are combined and precipitated with 1/10 volume of a 10 M solution of ammonium acetate and 2.5 volumes of ethanol. The amount of complementary DNA is 1 µg.

e) Hybridization

The residue of complementary DNA is suspended in 25 µl of TE buffer, 15 µg of RNA-poly A+ extracted from cells of the COS line are added, followed by 1/10 volume of a 3 M solution of NaCl and 2.5 volumes of ethanol, and the mixture is left to precipitate at −20° C.

It is centrifuged, the residue is washed with 70% ethanol, dried and dissolved in 5 µl of a buffer of the following composition: Tris-HCl 0.1 M pH 7.5, NaCl 0.3 M and EDTA 1 mM, the solution obtained is placed in a capillary tube, which is sealed, and incubation is then carried out at 65° C. for 40 h.

The contents of the capillary are diluted in 100 µl of TE buffer to which 300 µl of sodium phosphate buffer 50 mM pH 6.8 are added. The solution obtained is passed over a column of hydroxyapatite (Biorad, ref. 130.0520) at 60° C., equilibrated with this phosphate buffer. The single-stranded material (the unhybridized complementary DNA) and the double-stranded material (the COS messenger RNA hybridized with the complementary DNA) are separated by passing a gradient of 0.1 M to 0.2 M phosphate buffer through the column of hydroxyapatite. The fractions corresponding to the single-stranded complementary DNA are combined (25% by weight of the cDNA eluted, which corresponds to an approximately 4-fold enrichment in sequences specific for peripheral blood mononuclear cells), 20 μg of transfer RNA are added and the total volume is precipitated with 1/10 volume of a 10 M solution of ammonium acetate and 2.5 volumes of ethanol. The mixture is centrifuged, the residue is dissolved in 200 ml of TE, the residual phosphate is removed on polyacrylamide P10 and the solution is precipitated again with 1/10 volume of a 10 M solution of ammonium acetate and 2.5 volumes of ethanol.

The residue is dissolved in 30 μl of a solution of NaOH 30 mM, EDTA 2 mM. The complementary DNA is loaded on to a column of SEPHAROSE® CL4B (Pharmacia) of capacity 1 ml, equilibrated with a solution of NaOH 30 mM, EDTA 2 mM, in order to remove the remaining synthetic primer. The first 3 radioactive fractions, of about 80 μl each, are combined. The cDNA contained in these fractions is precipitated with 1/10 volume of a 10 M solution of ammonium acetate and 2.5 volumes of ethanol. The amount of complementary DNA recovered in this way is 20 ng.

f) Pairing of Cloning Vector pSE1 and the Complementary DNA in the Presence of the Adapter The mixture is centrifuged, the residue is dissolved in 33 μl of TE buffer, 5 μl (125 ng) of cloning vector pSE1, 1 μl (120 ng) of the adapter of the following sequence (SEQ ID NO:20) (comprising an ApaI site):

5' AAAAAAAAAAAAAGGGCCCG 3' and 10 μl of a 200 mM solution of NaCl are added, incubation is carried out for 5 min at 65° C. and the reaction mixture is then left to cool to room temperature.

g) Ligation

The cloning vector and the single-stranded cDNA are ligated in a volume of 100 μl with 32.5 units of the enzyme DNA ligase of phage T4 (Pharmacia, ref. 270 87002) overnight at 15° C.

h) Synthesis of the Second Strand of the cDNA

The proteins are removed by extraction with phenol followed by extraction with chloroform, and 1/10 volume of a 10 M solution of ammonium acetate and 2.5 volumes of ethanol are then added. The mixture is centrifuged and the residue is dissolved in a buffer of the following composition: Tris acetate pH 7.9 33 mM, potassium acetate 62.5 mM, magnesium acetate 1 mM and dithiothreitol (DTT) 1 mM. The second strand of complementary DNA is synthesized in a volume of 30 μl with 30 units of the enzyme DNA polymerase of phage T4 (Pharmacia: ref. 27-0718) and a mixture of the four deoxynucleotide triphosphates dATP, dCTP, dGTP and dTTP, as well as two units of the protein of the 32 gene of phage T4 (Pharmacia: ref. 27-0213), for 1 h at 37° C. Extraction is carried out with phenol and the traces of phenol are removed using a column of polyacrylamide P10 (Biogel P10-200-400 mesh—ref. 15011050—Biorad).

i) Transformation by Electroporation

E. coli MC1061 cells (Clontech) are transformed with the recombinant DNA obtained above by electroporation using a BIORAD GENE PULSER® apparatus (Biorad) run at 2.5 kV under the conditions prescribed by the manufacturer, and the bacteria are then grown for 6 h 30 min in so-called LB medium (Sambrook, op. cit.) of the following composition: bactotryptone 10 g/l, yeast extract 5 g/l and NaCl 10 g/l, to which 100 μg/ml of ampicillin have been added.

The number of independent clones is determined by plating a 1/1000 dilution of the transformation before amplification on a dish of LB medium to which 1.5% (w/v) of agar and 100 μg/ml of ampicillin have been added, this being called LB gelose medium hereafter. The number of independent clones is 500,000.

SECTION 3
Screening of the Subtracted Complementary DNA Library and Selection of Clone NC28

1) Creation of the Replicas of the Bacterial Colonies of the cDNA Library on a Nylon Filter About 40,000 recombinant bacteria of the cDNA library are distributed on (245×245) mm Petri dishes containing LB gelose medium (about 2000 colonies/dish).

Starting from each of these dishes, the colonies are transferred on to a nylon membrane (Hybond N-Amersham) by laying the membrane on the surface of the dish and making reference points by piercing the membrane with a needle. The membrane is then removed and laid on the surface of a new Petri dish containing LB gelose medium. This is left to stand for a few hours at 37° C. for regrowth of the colonies. Starting from this first membrane, two replicas are created on new membranes (moistened beforehand by being laid on LB gelose medium) by successive contacts with the first membrane. The resulting replicas on membranes are finally laid on dishes of LB gelose medium and incubated overnight at 30° C.

The replicas on membranes are laid, with the colonies facing upwards, on a sheet of Whatman 3MM saturated with a solution of the following composition: NaOH 0.5 M and NaCl 1.5 M, for 5 min, which makes it possible to lyze the bacteria and fix the DNA. The replicas on membranes are then placed on a second sheet of Whatman 3MM, saturated this time with a neutralizing solution of the following composition: NaCl 1.5 M and Tris-HCl pH 8 0.5 M, for 5 min. The replicas on membranes are then immersed in a 2×SSC solution (composition of the SSC solution: NaCl 0.15 M and sodium citrate 0.015 M) and the bacterial debris are partially removed by rubbing gently with cotton wool for cleaning.

The replicas on membranes are then treated with proteinase K (Boehringer Mannheim GmbH) at a concentration of 100 μg/ml in a solution of the following composition: Tris-HCl 10 mM pH 8, EDTA 10 mM, NaCl 50 mM and SDS 0.1%, at a rate of 20 ml per membrane. The mixture is incubated for 30 min at 37° C., with shaking. The replicas on membranes are reimmersed in a 2×SSC solution in order to remove definitively all traces of bacterial debris. Finally, they are dried for a few minutes on filter paper and then for 30 min under vacuum at +80° C. For each dish, this gives two replicas on membranes, hereafter called replica 1 and replica 2.

2) Preparation of the RNA Used to Produce the cDNA Probes a) Culture and Stimulation of the Single-Cell Line U937

The single-cell line U937 ATCC 1593 is cultivated in RPMI medium complemented with 10% of fetal calf serum (Gibco BRL—ref. 013-06290H), to which 10 units of penicillin and 10 μg of streptomycin have been added per ml and to which L-glutamine has been added to a final concentration of 2 mM. For activation of these cells, they are placed in RPMI medium to which penicillin, streptomycin, L-glutamine and 20 ng/ml of phorbol 2-myristate-3-acetate (PMA) (Sigma—ref. P8139) have been added, for 24 h. The cells activated in this way are scraped and centrifuged. The cell residue obtained is called cell residue U937P.

Half the cells are additionally induced with cycloheximide (10 μg/ml) during the last two hours of culture. This inhibitor of protein synthesis makes the unstable messenger RNAs (including the cytokinins) more stable (cf. T. Lindsten et al., 1989, Science, 244, 339–343). The cells activated in this way are scraped and centrifuged. The cell residue obtained is called cell residue U937PC.

b) Preparation of the RNA-poly $A^+$

Starting from cell residues U937P and U937PC, the RNA is extracted and the poly $A^+$ fraction is purified as described in section 1-2)a) and b). This gives two RNA-poly $A^+$ fractions, called poly A-1 fraction and poly $A^+2$ fraction respectively.

3) Preparation of the Radiolabeled cDNA Probes

The radiolabeled cDNA probes, called probe 1 and probe 2 respectively, are synthesized from the two RNA-poly $A^+$ fractions prepared above, in the manner described below.

1 μg of RNA-poly $A^+$ is hybridized with 200 ng of oligo $dT_{12-18}$ (Pharmacia) in 2 to 3 μl of a buffer of the following composition: Tris-HCl pH 7.5 50 mM and EDTA 1 mM, by incubation for 2 min at 65° C. and cooling to room temperature. The radiolabeled cDNA is synthesized in a reaction volume of 10 μl in a buffer of the following composition: Tris-HCl 50 mM pH 8.3, $MgCl_2$ 5 mM and dithiothreitol 10 mM, containing 50 μM dATP, dGTP and dTTP, 10 μM dCTP and 150 μCi of dCTP $\alpha^{32P}$ (3000 Ci/mmol, Amersham) and 40 units of RNasin (RNAse inhibitor—Genofit). The reaction is carried out at 46° C. for 30 min in the presence of 10 to 20 units of reverse transcriptase (Genofit). This synthesis is followed by alkaline hydrolysis of the RNA with a 0.3 M solution of NaOH in a final volume of 20 μl for 30 min at 65° C. The mixture is neutralized by the addition of 3 M acetic acid. The volume is adjusted to 50 μl with TE medium. Extraction is carried out with the same volume of phenol, this being followed by a second extraction with the same volume of a chloroform/isoamyl alcohol mixture (in the respective proportions 24/1). The dCTP $\alpha^{32P}$ not incorporated during the synthesis of the cDNA strand is removed by exclusion chromatography on a column of polyacrylamide P10 (Biogel-200-400 mesh—Biorad).

The amount of cDNA is 60 to 100 ng with a specific activity of $1 \times 10^9$ dpm/μg.

4) Hybridization of the Replicas of the Bacterial Colonies With the cDNA Probes

The replicas on membranes are prehybridized for 2 h at 42° C. in a buffer of the following composition: 50% formamide, 6×SSC, 5×Denhardt's solution, 0.1% SDS and 100 μg/ml of sonicated salmon sperm DNA, added after denaturation for 10 min at 100° C. The replicas on membranes are hybridized for two days: replica 1 with probe 1 and replica 2 with probe 2, these probes being used at a concentration of 4 ng/ml in the above buffer. The 5×Denhardt's solution (cf. Sambrook, op. cit.) has the following composition: FICOLL® (type 400—Pharmacia) 1 g/l, polyvinylpyrrolidone 1 g/l and bovine serum albumin (BSA) 1 g/l.

The prehybridization and hybridization are effected in tubes in a hybridizing oven (Hybaid) with 25 ml and 10 ml of buffer, respectively, per membrane.

The replicas on membranes are then successively washed several times for 15 min at 20° C. in a buffer of the following composition: 2×SSC and 0.1% SDS, and then twice for 15 min in a solution of the following composition: 0.1×SSC and 0.1% SDS, at 55° C., dried on Whatman 3MM paper and autoradiographed on Kodak XAR5 films.

5) Hybridization With a Mixture of Oligonucleotides Corresponding to the Majority of the Known Cytokinins To identify the clones which contain the DNAs complementary to the messenger RNAs of the known cytokinins, another series of replicas on membranes, prepared as described above, is hybridized with a mixture—called mixture C—of 28 oligonucleotides each containing 20 nucleotides, corresponding to the DNAs complementary to the following cytokinins: interleukin-1α (Furutani Y. et al., 1985, Nucl. Ac. Res., 13, 5869–5882), interleukin-1β (Auron P. et al., 1984, Proc. Natl. Acad. Sci. U.S.A., 81, 7907–7911), interleukin-2 (Degrave W. et al., 1983, EMBO J., 2, 3249–3253), interleukin-3 (Yang Y. C. et al., 1986, 47, 3–10), interleukin-4 (Yokoto T. et al., 1986, Proc. Ntl. Acad. Sci., 83, 5894–5898), interleukin-5 (Hirano T. et al., 1986, Nature, 324, 73–75), interleukin-6 (May L. et al., 1986, Proc. Natl. Acad. Sci. U.S.A., 83, 8957–8961), interleukin-7 (Namen A. et al., 1988, Nature, 333, 571–573), interleukin-8 (Matsushima K. et al., 1988, J. Exp. Med., 167, 1883–1893), interleukin-9 (Yang Y. C. et al., 1989, Blood, 74, 1880–1884), TNFα (Pennica D. et al., 1984, Nature, 312, 724–729), TNFβ (Gray P. et al., 1984, Nature, 312, 721–724), G-CSF (Nagata S. et al., 1986, 319, 415–418), M-CSF (Kawasaki E. et al., 1985, Science, 230, 291–296), GM-CSF (Wong G. et al., 1985, Science, 228, 810–815), LIF (Grough N. et al., 1988, Proc. Natl. Acad. Sci. U.S.A., 85, 2623–2627), interferon α (Goeddel D. et al., 1981, Nature, 290, 20–26), interferon β1(Taniguchi T. et al., 1980, Gene, 10, 11–15), interferon γ (Gray P. et al., 1982, Nature, 295, 503–508), TGFα (Derynck R. et al., 1984, Cell, 38, 287–297), TGFβ1 (Derynck R. et al., 1985, Nature, 316, 701–705), bFGF (Prats H. et al., 1989, Proc. Natl. Acad. Sci. U.S.A., 86, 1836–1840), erythropoietin (Jacobs K. et al., 1985, Nature, 313, 806–810), BCGF (Sharma S. et al., 1987, Science, 235, 1489–1492), MIF (Weiser W. et al., 1989, Proc. Natl. Acad. Sci. U.S.A., 86, 7522–7526), MCP-1 (Yoshimura T. et al., FEBS Lett., 244, 487–493), oncostatin-M (Malik N. et al., 1989, Mol. Cell. Biol., 9, 2847–2853) and EDF (Murata M. et al., 1988, Proc. Natl. Acad. Sci. U.S.A., 85, 2434–2438).

These oligonucleotides, produced using a BIOSEARCH 8700 DNA synthesizer, are coupled with horseradish peroxidase EC 1.11.17 (Boehringer Mannheim—ref. 814-407) according to the following protocol:

The oligonucleotides are reacted on the synthesis column with carbonyldiimidazole (Aldrich—11, 553-3) and 1,6-diaminohexane (Aldrich—H1.169-6) according to the method of Wachter et al., 1986, Nucl. Ac. Res., 14, 7985–7994.

After deprotection of the bases and cleavage of the support by ammoniacal treatment, the oligonucleotides are purified on an ion exchange resin (Quiagen—Diagen-500051), the ammonium counterion being changed to the lithium ion.

The 5'-aminooligonucleotides are coupled with horseradish peroxidase (Boehringer Mannheim—814407) according to the method of M. Urdea et al., Nucl. Ac. Res., 1988, 16, 4937–4956.

The mixture of oligonucleotides hybridizes with about 10% of the clones in the library.

The clones which give a stronger autoradiographic signal with probe 2 than with probe 1, and which do not hybridize with mixture C, were partially sequenced as described in section 4 below. One of these clones, called clone A in French patent application 90 14 961 and designated by clone NC28 in the present patent application, was retained.

SECTION 4

Sequencing and Analysis of the cDNA Sequence of Clone NC28

1) Sequencing of the cDNA of Clone NC28 a) Preparation of the Single-Stranded DNA

Clone NC28 contains vector pSE1, which carries a cDNA between the ApaI and BamHI sites, hereafter called NC28 cDNA.

Vector pSE1, which contains the origin of replication of phage f1, makes it possible to produce single-stranded DNA by culture of clone NC28 in the presence of bacteriophage M13K07 (Pharmacia—ref. 27-1524) in the following manner:

Clone NC28 is cultivated in a 15 ml tube, with shaking, at 37° C., in 2 ml of 2×YT medium of the following composition: bactotryptone 16 g/l, yeast extract 10 g/l and NaCl 5 g/l (described in Sambrook et al., op. cit.), complemented with 0.001% of thiamine and 100 µg/ml of ampicillin, to an optical density of about 0.60 at 660 nm.

100 µl of this culture are infected with bacteriophage M13K07 (Pharmacia—ref. 27-1524) at a multiplicity of infection of the order of 10, in a 15 ml tube. The culture is shaken at 37° C.

After 1 h, 2 ml of medium are added. The culture is then incubated for about 16 h at 37° C., with shaking.

1.5 ml of the culture are centrifuged in a microtube at 15,000 g for 2 min.

1 ml of supernatant is transferred to a microtube and 250 µl of a 20% solution of polyethylene glycol (of molecular weight 6000), containing 2.5 M NaCl, are added. The mixture is incubated for 5 min at 4° C. to facilitate precipitation of the phage, and then centrifuged for 5 min at 15,000 g. The supernatant is removed and the residue of phage is resuspended in 500 µl of a buffer of the following composition: Tris-HCl 10 mM pH 8 and EDTA 1 mM.

The suspension is extracted once with phenol saturated with Tris-HCl 100 mM pH 8, and then twice with chloroform.

The preparation is then precipitated by the addition of 1/10 volume of a solution of sodium acetate 3 M pH 4.8 and 2.5 volumes of ethanol. Precipitation is effected at −20° C. for a minimum of 20 min. The DNA is centrifuged for 10 min at 15,000 g and the residue is washed with a 70% solution of ethanol and then resuspended in 30 µl of a buffer of the following composition: Tris-HCl 10 mM pH 8 and EDTA 1 mM.

b) Sequencing

The sequencing reactions are carried out with the aid of a United States Biochemical sequencing kit (ref. 70770), which uses the method of Sanger et al., Proc. Ntl. Acad. Sci. U.S.A., 1977, 14, 5463–5467. The primers used are oligonucleotides of 18 nucleotides, which are complementary either to vector pSE1 in the region immediately at the 5' end of NC28 cDNA, or to the sequence of NC28 cDNA.

2) Analysis of the Sequence of NC28 cDNA

The following description will be understood more clearly with the aid of FIGS. 2, 3 and 4.

FIG. 2 shows the nucleotide sequence of NC28 cDNA (SEQ ID NO:15) and, underneath, the translated amino acid sequence (SEQ ID NO:16), the three Met capable of initiating translation being underlined, the N-glycosylation site being underlined with a broken line and the probable cleavage site of the signal peptide being indicated by a vertical arrow.

FIG. 3 and FIG. 4 respectively show the maximum homology alignment, according to the method of Needleman and Wunsch, 1970, J. Mol. Biol., 48, 443–453, of the amino acid sequence translated from NC28 cDNA (upper line, SEQ ID NO:16) and of the amino acid sequence translated from the cDNA of the cytokinin MCP-1 (lower line, SEQ ID NO:24), and the alignment, according to this method, of NC28 cDNA (upper line, bases 1-800 of SEQ ID NO:15) and of the cDNA of the cytokinin MCP-1 (lower line, SEQ ID NO:25).

Analysis of the Sequence of NC28 cDNA (1) (SEQ ID NO:15) NC28 cDNA contains 804 nucleotides and terminates with a poly A sequence.

(2) This number of nucleotides is in agreement with the size of the corresponding messenger RNA (about 0.8 kb), measured by electrophoresis on 1% agarose gel in the presence of formaldehyde (Sambrook, op. cit.), followed by transfer to a nylon membrane (Hybond N+—Amersham) and hybridization according to the protocol described below.

This membrane is hybridized with a probe radiolabeled with $^{32}$P-dCTP (Amersham), produced from NC28 cDNA by partial cleavage of the latter with DNAse I, followed by polymerization with the aid of the enzyme DNA polymerase I (a technique known as nick translation), as described by Sambrook et al., op. cit. The hybridization takes place at 42° C. for 16 h in an aqueous medium containing 50% of formamide, 1 M NaCl, a 5×Denhardt's solution and 0.1% of SDS. The membranes are washed several times at room temperature with a 2×SSC solution containing 0.1% of SDS, and then washed twice at 50° C. for 15 min with a 0.1×SSC solution containing 0.1% of SDS. The 5×Denhardt's solution has the following composition: Ficoll (type 400—Pharmacia) 1 g/l, polyvinylpyrrolidone 1 g/l and BSA 1 g/l. The 1×SSC solution contains 0.15 M NaCl and 0.015 M sodium citrate.

(3) In position 787-792, the sequence CATAAA, which resembles the consensus sequence AATAAA described by M. Birnstiel et al., 1985, Cell, 41, 349, is probably a polyadenylation signal. In position 534-554, of SEQ ID NO:15 a region rich in A and T—TTATTAATATTTTAATTTAAT—contains the instability consensus pattern ATTTA described by G. Shaw et al., 1986, Cell, 46, 659–667. The majority of the known cytokinins possess such a region rich in A and T, which contains this instability consensus pattern.

(4) The DNA sequence contains an open reading frame for the translation of a protein from the ATG in position 41-43 to the TGA in position 368–370 of SEQ ID NO:15, which corresponds to a translation stop codon. In this reading frame, there are three ATG codons in positions 41-43, 53-55 and 71-73 of SEQ ID NO:15, capable of initiating translation. Among these, the nucleotide environment of the ATG in positions 71-73 is the one most similar to the consensus sequence described by Kozak M., 1978, Cell, 15, 1109–1123, for initiating translation in eucaryotic cells.

(5) A signal peptide search software, hereafter called PS software, has been developed by the Applicant following the method and information described by Von Heijne, 1986, Nucl. Ac. Res., 14, 483–490. This software anticipates, in this reading frame, a hydrophobic region resembling a signal peptide and a probable protein cleavage site in position 139-140 (between Ala and Gln). The anticipated signal peptide is between one of the three Met capable of initiating translation, and this cleavage site. The mature protein (translated protein cleaved from its signal peptide) therefore comprises 76 amino acids (cf. FIG. 2).

(6) The amino acid sequence of the protein translated from NC28 cDNA (SEQ ID NO:16) and the sequence of NC28 cDNA (SEQ ID NO:15) were respectively compared with the sequence of the protein translated from the cDNA of the cytokinin MCP-1 and with the sequence of the cDNA of the cytokinin MCP-1 using an appropriate software, namely the UWGCG software from the University of Wisconsin: Devereux et al., 1984, Nucl. Ac. Res., 12, 8711–8721—Option GAP: optimal sequence alignment according to the method of Needleman and Wunsch, 1970, J. Mol. Biol., 48, 443–453. This comparison showed about 74% identity between the amino acid sequence of the protein translated from NC28 cDNA and the sequence of the cytokinin MCP-1 (73 out of the 99 amino acids were identical) and about 79% identity between the part of NC28 cDNA coding for the translated protein and the cDNA of the cytokinin MCP-1 (235 out of the 297 nucleotides were identical).

The cleavage site predicted by the PS software, in position 139-140 (between Ala and Gln), corresponds to that found experimentally for the cytokinin MCP-1 by E. Robinson et al., 1989, Proc. Ntl. Acad. Sci. U.S.A., 86, 1850–1854. The ATG in position 71-73 of NC28 cDNA corresponds to the translation initiation ATG of the cytokinin MCP-1.

The homology between the amino acid sequence of the protein translated from NC28 cDNA (SEQ ID NO:16) and the sequence of the cytokinin MCP-1 indicates that the protein translated from NC28 cDNA is a secreted protein of the cytokinin type.

SECTION 5
Analysis of the Secretion in COS Cells of the Protein Coded by NC28 cDNA COS cells are monkey kidney cells expressing SV40 T-antigen (Gluzman Y., Cell, 23, 1981, 175–182). These cells, which permit the replication of vectors containing the origin of replication of SV40 DNA (the case of vector pSE1), constitute preferred hosts for studying the expression of genes in animal cells.

1) Transfection of COS Cells and Transitory Expression of the Protein Coded by NC28 cDNA $5 \times 10^5$ COS cells are inoculated in a Petri dish of diameter 6 cm (Corning) in 5 ml of Dulbecco's Modified Eagle's Medium (Gibco, ref. 041-01965), hereafter called DMEM, which contains 0.6 g/l of glutamine and 3.7 g/l of NaHCO, and is complemented with fetal calf serum (Gibco) at a rate of 5%. After culture for about 16 h at 37° C. in an atmosphere containing 5% of carbon dioxide, the culture medium is sucked off and the cells are washed with 3 ml of PBS (Phosphate Buffered Saline from GIBCO). The following mixture is then added: 1000 μl of (DMEM+10% fetal calf serum (Gibco)), 110 μl of diethylaminoethyldextran of average molecular weight 500,000 (Pharmacia), at a concentration of 2 mg/ml, 1.1 μl of chloroquine 100 mM (Sigma) and 6 μg of plasmid DNA of clone NC28, prepared by the technique of alkaline lysis followed by purification of the plasmid DNA on a cesium chloride gradient (Sambrook et al., op. cit.). After incubation for 5 h at 37° C. in an atmosphere containing 5% of carbon dioxide, the mixture is withdrawn from the cells. 2 ml of PBS containing 10% of dimethyl sulfoxide (spectroscopic grade, Merck) are then added. After incubation for 1 min at room temperature, the mixture is withdrawn and the cells are washed twice with PBS and incubated in DMEM containing 2% of fetal calf serum. Incubation is continued for 40 h at 37° C. under an atmosphere containing 5% of carbon dioxide.

Also, control COS cells were prepared by carrying out the above-described operations with the DNA of plasmid pSE1.

2) Labeling of the Proteins

The operations described below are all performed with COS cells transfected by the plasmid DNA of clone NC28 and with control COS cells.

The culture medium is sucked off and the cells are washed twice with 3 ml of PBS. 5 ml of MEM (Eagle's Minimum Essential Medium) without methionine (Gibco—ref. 041-01900H), complemented with 3 g/ml of glucose and 4 mM glutamine, are added. Incubation is carried out for 2 h at 37° C. The culture medium is removed and a further 2 ml of the same medium, to which 200 μmCi of methionine 35S (ref. SJ1015, Amersham) have been added, are added to the cells. Incubation is carried out for 6 h at 37° C. The culture medium is removed and centrifuged for 5 min to eliminate the cell debris and suspended cells, and the supernatant is retained. The adhesive cells are rinsed twice with PBS, scraped with a rubber scraper and centrifuged.

3) Analysis of the Radiolabeled Proteins of the Transfected COS Cells by Polyacrylamide Gel Electrophoresis 1 ml of the supernatant of the transfected COS cells and 9 ml of acetone are precipitated at −20° C. The mixture is centrifuged and the protein residues are recovered. They are taken up in a buffer of following composition: Tris 0.125 M pH 6.8, SDS 4% and glycerol 20%. An aliquot of the resulting suspension, corresponding to a radioactivity of 200,000 cpm, is analyzed by electrophoresis on a 15% polyacrylamide gel in the presence of SDS according to the technique described by U.K. Laemmli, Anal. Biochem., 1977, 78, 459. The gel is dried under vacuum. The radiolabeled proteins are developed by autoradiography.

The autoradiograph shows the presence of four extra bands for the cells transfected by the plasmid DNA of clone NC28, compared with the control cells: two high-intensity bands corresponding to apparent molecular weights of 9±2 and 16±2 kDa and two low-intensity bands corresponding to apparent molecular weights of 11±2 and 17±2 kDa (the latter band is diffuse). The molecular weight calculated for the mature protein of 76 amino acids is 8956 Da, i.e. similar to the apparent molecular weight corresponding to the first of these bands.

The different bands observed, or some of them, may correspond to various degrees of glycosylation of the protein of the invention. The latter (cf. FIG. 2) in fact has an asparagine residue capable of being N-glycosylated (underlined with a broken line in FIG. 2 and corresponding to the consensus sequence described by DONNER et al., J. Cell. Biol., 1987, 105, 2665) and several serine and threonine residues capable of being O-glycosylated.

4) Demonstration of the Probable N-glycosylation of the Forms With Apparent Molecular Weights of 16±2 and 17±2 kDa The proteins are labeled as in 2) above, but in the presence of 10 mg/ml of tunicamycin (Sigma—ref. T7765), which is a protein N-glycosylation inhibitor.

The analysis of the proteins on polyacrylamide gel is performed as in 3).

The autoradiograph shows the presence of two extra bands for the cells transfected by the plasmid DNA of clone NC28, compared with the control cells: one high-intensity band corresponding to an apparent molecular weight of 9±2 kDa and one low-intensity band corresponding to an apparent molecular weight of 11±2 kDa. These results show that the two forms of the recombinant protein observed in 3), corresponding to molecular weights of 16±2 and 17±2 kDa, are N-glycosylated.

SECTION 6
Purification of the Recombinant Protein Secreted by COS Cells

1) Production of the Recombinant Protein $4 \times 10^7$ COS cells are inoculated in a cylindrical culture flask, usually called a roller, with a surface area of 850 cm$^2$, in 150 ml of Dulbecco's Modified Eagle's Medium (Gibco, ref. 041-01965), hereafter called DMEM, which contains 0.6 g/l of glutamine and 3.7 g/l of $NaHCO_3$ and is complemented with fetal calf serum (Gibco) at a rate of 5% and then buffered with carbon dioxide. After culture for about 16 h at 37° C. with a speed of rotation of about 0.2 rpm, the culture medium is sucked off and the cells are washed with PBS (Phosphate Buffered Saline from Gibco). The following mixture is then added: 36 ml of (DMEM+10% fetal calf serum (Gibco)), 4 ml of diethylaminoethyl-dextran of average molecular weight 500,000 (Pharmacia), at a concentration of 2 mg/ml, 40 μl of chloroquine 100 mM (Sigma) and 128 μg of the plasmid DNA of clone NC28, prepared by the technique of alkaline lysis followed by purification of the plasmid DNA on a cesium chloride gradient (Sambrook et al., op. cit.). After incubation for 5 h at 37° C. in an atmosphere containing 5% of carbon dioxide, the mixture is withdrawn from the cells. 35 ml of PBS containing 7% of dimethyl sulfoxide (spectroscopic grade, Merck) are then added. After rotation for 1 min 30 s at room temperature, the mixture is withdrawn and the cells are washed twice with PBS and incubated for 5 days at 37° C., with rotation, in DMEM without phenol red. The supernatant, which has a volume of about 130 ml, is removed.

2) Isolation and Purification of the Recombinant Protein

The recombinant protein was isolated and purified from the supernatant obtained above, with the following successive steps:

Ion exchange chromatography on a DEAE-Sepharose column (Pharmacia) equilibrated beforehand with a solution of Tris-HCl 50 mM pH 8.0. Under these operating conditions, the protein does not bind to the gel.

Affinity chromatography on a column of heparin Sepharose (Pharmacia) equilibrated beforehand with a solution of Tris-HCl 50 mM pH 8, using a linear gradient of 0 to 1 M NaCl in a solution of Tris-HCl 50 mM pH 8.0 as the eluent.

Dialysis of the fractions containing the recombinant protein, whose degree of purity, determined by electrophoretic analysis on polyacrylamide gel in the presence of SDS and developing with silver nitrate, is more than 90%, either against a solution of PBS for the sample subjected to the test for chemotaxis described in section 11, or against a solution, called solution 1, of MOPS buffer 20 mM pH 6.4, containing 0.1 M NaCl, for the chromatography step below.

Cation exchange chromatography of these fractions on a MONO S® HR 5/5 column (Pharmacia) equilibrated beforehand with solution 1, using a linear gradient of 0.1 to 0.4 M NaCl in solution 1 as the eluent (for 60 min) and with detection at 280 nm.

The recombinant protein is present in the fractions corresponding to two peaks, called fraction 1 and fraction 2, which, on electrophoretic analysis in the presence of SDS, respectively give a majority band with an apparent molecular weight of 9±2 kDa and a minority band with an apparent molecular weight of 11±2 kDa in one case, and a majority band with an apparent molecular weight of 16±2 kDa and a series of weak bands with apparent molecular weights of between (16 and 18)±2 kDa in the other case.

Analysis of each of these two fractions by polyacrylamide gel electrophoresis in the presence of SDS and developing with silver nitrate does not reveal bands other than the forms of protein NC28 described above, showing that the recombinant protein has a degree of purity of at least 95% in each of the fractions.

3) Analysis of the Amino-Terminal Sequence of Each of Fractions 1 and 2

For each of fractions 1 and 2, the amino-terminal sequence was analyzed using an Applied Biosystem model 470A sequencer coupled with an Applied Biosystem model 120A analyzer of phenylthiohydantoic derivatives. The purified protein (200 pmol, checked by amino acid analysis) was deposited on the sequencer in the presence of 20 pmol of the control protein β-lactoglobulin.

No amino-terminal sequence corresponding to the amino acid sequence coded by NC28 cDNA was detected (by contrast, the amino-terminal sequence of the control protein was detected, indicating that the sequencer was working).

There is therefore probably amino-terminal blocking of each of the different forms of the recombinant protein.

4) Study of the Glycosylation of the Different Forms of Protein NC28

Fractions 1 and 2 were digested with the 3 enzymes N-glycanase, neuraminidase and O-glycanase (Genzyme) following the protocol described in the data sheet supplied with these enzymes.

The products of these enzymatic digestions were analyzed by electrophoresis in the presence of SDS according to the technique of Laemmli U.K., 1977, Anal. Biochem., 78, 459. The results are as follows:

The majority band with an apparent molecular weight of 9±2 kDa is not modified in the presence of N-glycanase, neuraminidase or O-glycanase.

The minority band with an apparent molecular weight of 11±2 kDa is not modified by N-glycanase but is modified by neuraminidase to give a band with an apparent molecular weight of 10±2 kDa, this band itself being modified by O-glycanase to give a band identical to the majority band with an apparent molecular weight of 9±2 kDa.

The majority band with an apparent molecular weight of 16±2 kDa is not modified by neuraminidase or O-glycanase but, after the action of N-glycanase, it is identical to the majority band with an apparent molecular weight of 9±2 kDa.

The bands with apparent molecular weights of between (16 and 18)±2 kDa disappear under the action of each of the three enzymes.

These experiments show that the majority form with an apparent molecular weight of 9±2 kDa is a non-glycosylated form of protein NC28, the minority form with an apparent molecular weight of 11±2 kDa is an O-glycosylated form of protein NC28 containing 1 or more sialic acids, and the majority form with an apparent molecular weight of 16±2 kDa is an N-glycosylated form of protein NC28.

The minority forms with apparent molecular weights of between 16 and 18 kDa probably represent a complex mixture of N- and O-glycosylated forms.

Protein NC28 is the first known member of the family of the human SIS cytokinins which is N-glycosylated (A. Minty, 1991, Medecine Sciences, 7, 578). The cytokinin MCP-1 exists in an O-glycosylated form but not in an N-glycosylated form (Jiang et al., 1990, J. Biol. Chem., 30, 18318).

SECTION 7

Construction of an Expression Vector for NC28 cDNA in Yeast: Plasmid pEMR617 and Transformation of a Yeast Strain Using This Plasmid 1) Construction of Plasmid pEMR617

Plasmid pEMR583 (described in European patent application 435776) was subjected to complete digestion with the enzymes HindIII and BamHI. The large fragment (hereafter called fragment A), comprising the 2 micron origin of replication and STB locus, the LEU2d gene, the ampicillin resistance gene, the origin of pBR322, the terminator of the PGK gene, the URA3 gene, the artificial promoter and the start of the prepro region of pheromone alpha, was purified.

The HindIII-BamHI fragment (hereafter called fragment B), comprising the end of the prepro region of pheromone alpha and the cDNA coding for the mature protein, flanked by the BamHI restriction site at the 3' end, was obtained by amplification using the PCR technique starting from plasmid pSE1-NC28. The sequence of this fragment is detailed in FIG. 5. Fragments A and B were ligated to give plasmid pEMR617.

a) Description of the Polymerase Chain Reaction (PCR) Technique

The polymerase chain reaction (PCR) technique is a method well known to those skilled in the art, which makes it possible simultaneously to copy the two strands of a previously denatured DNA sequence using two oligonucleotides as primers (cf. especially the work by H. A. Erlich: "PCR Technology: Principles and Applications for DNA Amplification" published in 1989 by Macmillan Publishers Ltd, United Kingdom, and the work by M. A. Innis et al.: "PCR Protocols" published in 1990 by Academic Press Inc., San Diego, Calif. 92101, U.S.A.). The principle of this technique is summarized below.

The PCR technique is based on the repetition of three steps, which makes it possible, after between 10 and 30 cycles, to obtain hundreds of thousands of copies of the original template, using a DNA polymerase of Thermus aquaticus, usually referred to as Taq poly-merase. The three steps are as follows:

Denaturation of the Template

The double-stranded DNA is denatured to single-stranded DNA by incubation at high temperature (from 92° C. to 96° C.) for approximately 2 min.

Hybridization of the Primers

These primers are a pair of synthetic oligo-nucleotides which hybridize with the ends of the region to be amplified. The two primers hybridize with the opposing strands. The primers are added in excess so as to favor the formation of the primer-template complex.

Extension of the Primers

The step in which the Taq polymerase extends the primer-template complex from the 5' end to the 3' end is carried out at 72° C.

In the PCR technique, the product of interest appears in the third cycle and is then amplified significantly. In the course of the cycles, the amplification product rapidly becomes the template with which the primers hybridize.

b) Description of the Primers Used

Two synthetic oligonucleotides were prepared.

The first oligonucleotide, referred to as primer 1, which has the following sequence (SEQ ID NO:21):

```
ATCGA AGC TTG GAT AAA AGA   CAG CCA GTT GGG ATT AAT AC
      Ser Leu Asp Lys Arg   Gln Pro Val Gly Ile Asn
          Region 1                  Region 2
``` possesses two distinct regions: region 1, which contains the end of the prepro region of pheromone a modified relative to the natural sequence described by Kurjan et al., Cell, 1982, 30, 933–943, by a silent mutation which makes it possible to introduce a HindIII site just before the coding part of region 1 (fifth nucleotide of region 1), and region 2, a region which is intended to hybridize with the coding region corresponding to the start of the mature protein of 76 amino acids (cf. section 4) of the non-coding strand of that part of plasmid pSE1-NC28 which carries NC28 cDNA.

The second oligonucleotide, referred to as primer 2, which has the following sequence (SEQ ID NO:23):

```
CAGTGGATCC    TCAAAGTTTTGGAGTTTGGG
  Region 1           Region 2
``` also consists of two distinct regions: region 1, which carries a BamHI site on the fifth nucleotide, and region 2, which carries a nucleotide sequence corresponding to the last codons of the coding part of NC28 cDNA and to the stop codon, with a mutation which is intended to eliminate the HindIII site (silent mutation of codon AAG to AAA). This region is intended to hybridize with the coding strand of that part of plasmid pSE1-NC28 which carries NC28 cDNA.

c) Preparation of the HindIII-BamHI Amplified Fragment Representing the End of the Prepro Region of Pheromone α and the cDNA Coding for Mature Protein NC28

The template used is plasmid pSE1-NC28, which carries the cDNA coding for protein NC28.

100ng of plasmid pSE1-NC28, 100 ng of primer 1, 100 ng of primer 2 and 5 µl of 10-fold concentrated reaction mixture (final amount: 67 mM Tris-HCl pH 8.8, 16.6 mM $(NH_4)_2SO_4$, 1 mM β-mercaptoethanol, 6.7 mM EDTA, 0.15% Triton×100, 2 mM $MgCl_2$, 0.2 mM dNTP, 200 ng of gelatin) are placed in a tube and the volume of the mixture is then made up to 50 ml by the addition of water.

0.5 µl, i.e. 2.5 units, of Taq polymerase (Boehringer Mannheim ref. 1146-173) is added. The mixture is then covered with paraffin to prevent evaporation of the aqueous solution.

Amplification takes place over 15 reaction cycles, the steps of one cycle being as follows:

1 min at 94° C.→denaturation
1 min at 55° C.→hybridization
1 min at 72° C.→polymerization After the 15 cycles, the enzymatic reaction is stopped by the addition of 20 mM EDTA.

The DNA fragment amplified in this way, which has the expected size of about 250 bp, is then isolated and purified on 1% agarose gel, dialyzed by chromatography on a column of P10 polyacrylamide gel (Pharmacia) and then hydrolyzed totally and simultaneously with the enzymes HindIII and BamHI by the customary techniques well known to those skilled in the art (Sambrook et al., op. cit.) so as to form the HindIII and BamHI sticky ends. After hydrolysis, the fragment is purified on a Plo column.

The sequence of the fragment B obtained is shown in FIG. 5 (SEQ ID NO:17). In its part coding for protein NC28, it comprises a silent mutation relative to NC28 cDNA, indicated by an asterisk in FIG. 5.

Fragments A and B were ligated to give plasmid pEMR617.

2) Transformation of the Yeast Strain EMY761 With Plasmid pEMR617 and Expression of Protein NC28 by the Transformed Strain The strain EMY761 (Mat alpha, leu2, ura3, his3) described in European patent 0408461, which can be obtained by plasmid curing of the strain deposited in the CNCM on 27th December 1989 under no. I-1021, contains mutations (leu2 and ura3) which are capable of being complemented by the LEU2d defective selection marker and URA3 selection marker present in plasmid pEMR617. It was transformed with plasmid pEMR617, with selection for the prototrophy of leucine, using a variant of the transformation technique described by Beggs et al. (Beggs et al., 1978, Nature 275, 104–109), which consists in subjecting the yeasts to a protoplastization treatment in the presence of an osmotic stabilizer, namely sorbitol at a concentration of 1 M.

The precise transformation protocol is indicated below:

a) 200 ml of liquid YPG medium (cf. Table 1 below) are inoculated with about $5\times10^6$ cells of a culture in the stationary phase, and the culture inoculated in this way is shaken overnight at 30° C.

b) When the culture reaches about $10^7$ cells per ml, the cells are centrifuged at 4000 rpm for 5 min and the residue is washed with a 1 M solution of sorbitol.

c) The cells are suspended in 5 ml of 1 M sorbitol solution containing 25 mM EDTA and 50 mM dithiothreitol, and incubated for 10 min at 30° C.

d) The cells are washed once with 10 ml of 1 M sorbitol solution and suspended in 20 ml of sorbitol solution. ZYMOLASE®-100T (a preparation marketed by Seykagaku Kogyo Co. Ltd., obtained by partial purification of *Arthobacter luteus* culture supernatant on an affinity column and containing β-1,3-glucanaselaminaripentahydrolase) is added to a final concentration of 20 µg/ml and the suspension is incubated at room temperature for about 15 min.

e) The cells are resuspended in 20 ml of a sorbitol-containing medium called YPG sorbitol medium (cf. Table 1 below) and incubated for 20 min at 30° C., with gentle shaking.

f) The suspension is centrifuged for 3 min at 2500 rpm.

g) The cells are resuspended in 9 ml of a transformation buffer of the following composition: sorbitol 1 M, Tris-HCl pH 7.5 10 mM and $CaCl_2$ 10 mM).

h) 0.1 ml of cells and 5 µl of DNA solution (about 5 mg) are added and the suspension obtained is left for 10 to 15 min at room temperature.

i) 1 ml of the following solution is added: polyethylene glycol PEG 4000 20%, Tris-HCl 10 mM pH 7.5 and $CaCl_2$ 10 mM.

j) 0.1 ml of the suspension obtained in i) is poured into a tube containing leucine-free solid regeneration medium (cf. Table 1 below) which has been melted beforehand and kept liquid at about 45° C. The suspension is poured into a Petri dish containing a solidified layer of 15 ml of leucine-free solid regeneration medium.

The transformants start to appear after three days. A transformant called strain EMY761 pEMR617 was thus obtained.

Table 1

Composition and Preparation of the Principal Media Used in the Protocol for Transformation of the Yeast Strain EMY761

Liquid YPG Medium 10 g of yeast extract (Bacto-yeast extract from Difco)

20 g of peptone (Bacto-peptone from Difco)

20 g of glucose

Mix the ingredients in distilled water. Make up to a final volume of 1 l with distilled water. Autoclave for 15 min at 120° C.

YPG Sorbitol Medium

Use the formulation of the liquid YPG medium and, after autoclaving, add sorbitol to a concentration of 1 M.

Leucine-Free Solid Regeneration Medium 6.7 g of yeast nitrogen base without amino acids (from Difco)

20 mg of adenine 20 mg of uracil 20 mg of L-tryptophan 20 mg of L-histidine 20 mg of L-arginine 20 mg of L-methionine 30 mg of L-tyrosine 30 mg of L-isoleucine 30 mg of L-lysine 50 mg of L-phenylalanine 100 mg of L-glutamic acid 150 mg of L-valine 20 g of glucose 30 g of agar 182 g of sorbitol Mix all the ingredients in distilled water. Make up to a final volume of 1 l with distilled water. Autoclave for 15 min at 120° C. After autoclaving, add 200 mg of L-threonine and 100 mg of L-aspartic acid.

SECTION 8

Expression, in an Erlenmeyer Flask, of Protein NC28 by the Transformed Yeast Strain and Detection of the Protein in the Culture Medium on Polyacrylamide Gel in the Presence of SDS 1) Culture of the Strain EMY761 pEMR617

A colony of the strain EMY761 pEMR617 (obtained in section 7) was cultured in 50 ml of uracil-free liquid medium. This medium contains the following per liter:

6.7 g of yeast nitrogen base without amino acids (from Difco)

5.0 g of casein hydrolysate (casamino acids from Difco)

10 g of glucose

After one night at 30° C., with shaking, the culture was centrifuged for 10 min and the residue was taken up in 10 ml of sterile water and centrifuged again for 10 min. The expression of protein NC28 was induced by taking up the cells in 50 ml of a medium of the following composition:

6.7 g/l of yeast nitrogen base without amino acids (from Difco)

5.0 g/l of casein hydrolyzate (casamino acids from Difco)

30.0 g/l of glycerol 30.0 g/l of galactose 10 ml/l of ethanol

The culture was reincubated at 30° C. for 24 h, with shaking.

2) Analysis of the Expressed Protein a) Polyacrylamide Gel in the Presence of SDS Preparation of the Samples Some of the cells cultivated overnight in a medium called uracil-free liquid medium with glucose, the composition of which is specified in Table 2 below, were centrifuged to give a non-induced sample. The cells cultivated overnight in a medium called uracil-free liquid medium with ethanol, glycerol and galactose (Table 2 below) were centrifuged to give an induced sample. The supernatant was collected. 5 ml of 50% trichloroacetic acid containing 2 mg/ml of deoxycholate were added to 10 ml of supernatant.

The mixture was left at a temperature of +40° C. for 30 min and then centrifuged for 30 min. The residue was taken up in about 1 ml of cold acetone (+4° C.) and centrifuged again for 30 min. After drying, the residue is taken up in about 20 µl of a so-called loading buffer consisting of Tris-HCl 0.125 M pH 6.8, SDS 4%, bromophenol blue 0.002%, glycerol 20% and β-mercaptoethanol 10%, according to the protocol described by Laemmli (op. cit.). The residue is solubilized by boiling for 15 min and then neutralized until the bromophenol blue turns blue.

The samples are deposited on a polyacrylamide gel in the presence of SDS and subjected to electrophoresis.

Results

Analysis of the gel (developing with Coomassie blue) shows the presence of several additional bands for the induced sample compared with the non-induced sample, the two main additional bands corresponding to an apparent molecular weight of 9±2 (majority form) and 11±2 kDa. The other additional bands observed, with an apparent molecular weight of more than 16±2 kDa, which are fairly numerous and diffuse, probably correspond to a variable degree of glycosylation. A band of low intensity is also observed, corresponding to an apparent molecular weight of 8 kDa.

It is known that the N-glycosylation of a protein with yeast involves a simple N-glycosylation (core glycosylation) in the endoplasmic reticulum and an N-hyperglycosylation (outer-chain glycosylation) in the Golgi apparatus (R. A. Hitzeman et al., 1990, "Methods in Enzymology, no. 185", Academic Press, p. 421–440). In general, core glycosylation produces a glycoprotein of homogeneous apparent molecular weight (one band) and outer-chain glycosylation produces a glycoprotein of heterogeneous apparent molecular weight (several diffuse bands). It is also known that certain proteins can be O-glycosylated by yeast (J. Zueco et al., 1986, Biochemica et Biophysica Acta, 884, 93–100).

N-Glycosylation can be demonstrated in several ways (P. Oleans et al., 1991, Methods in Enzymology, 194, 682–697), one of which consists in observing the decrease in the apparent molecular weight of the protein when it is treated with endoglycosidase H (endo-b-N-acetylglucosaminidase: E. C. 32.1.96), which specifically cleaves N-bonded carbohydrate chains. O-Glyco-sylation can be assumed when the protein is resistant to endoglycosidase H and when its apparent molecular weight decreases after treatment with α-mannosidase (α-D-mannoside mannohydrolase: E. C. 3.2.1.24), as described by Biemans et al., 1991, DNA and Cell Biology, 10, 191–200.

b) Immunoblotting (Western Blot) With Possible Endoglycosidase H Treatment

Preparation of the Samples

Some of the cells cultivated overnight in uracil-free liquid medium with glucose (Table 2) were centrifuged to give a non-induced sample. The cells cultivated overnight in uracil-free liquid medium with ethanol, glycerol and galactose (Table 2) were centrifuged to give an induced sample. The supernatant was collected. 5 ml of 50% trichloroacetic acid containing 2 mg/ml of deoxycholate were added to 10 ml of supernatant.

The mixture was left at a temperature of 4° C. for 30 min and then centrifuged for 30 min. The residue was taken up in about 1 ml of cold acetone (+4° C.) and centrifuged again for 30 min. The residue is taken up in 40 μl of a solubilization buffer (composition: Tris-HCl pH 6.8 10 mM, β-mercaptoethanol 2%, SDS 1%). The residue is heated at 100° C. for 15 min.

The sample is then divided up into four fractions:

10 μl of a sodium citrate buffer 50 mM pH 5 and 5 μl of endoglycosidase H (5 mIU—Boehringer ref. 1088726) are added to the first 10 μl fraction. The sample is left at 37° C. for about 1 night. 20 μl of loading buffer are then added.

10 μl of sodium citrate buffer 50 mM pH 5 and 2.5 μl of α-mannosidase (Sigma ref. M7257) are added to the second 10 pi fraction. The sample is left at 37° C. for about 1 night. 20 μl of loading buffer are then added.

10 μl of sodium citrate buffer 50 mM pH 5 and 5 μl of endoglycosidase H (Boehringer) are added to the third 10 μl fraction. The sample is left at 37° C. for about 1 night. 2.5 μl of α-mannosidase (Sigma) are then added. The sample is left at 37° C. overnight. 20 μl of loading buffer are added.

10 μl of loading buffer are added to the fourth 10 μl fraction. The samples are boiled for 10 min and deposited on polyacrylamide gel in the presence of SDS and electrophoresis is carried out according to the protocol of Laemmli, Anal. Biochem., 1977, 78, 459.

The proteins contained in the gel are then transferred to a nitrocellulose membrane (by the technique of H. Towbin et al., 1979, Proc. Natl. Acad. Sci. U.S.A., 76, 4350–4354). Immunodetection, performed according to the protocol described in the Immuno-Blot Assay Kit from Bio-Rad (ref. 170-6450), involves the following steps:

saturation of the nitrocellulose membrane for 30 min with TBS (Tris Buffered Saline) containing 3 g/100 ml of gelatin;

rinsing of the membrane twice for 5 min with a buffer called T.TBS (TBS containing 0.05% of Tween 20);

bringing of the membrane into contact, for 1 h at room temperature, with the immune serum prepared in section 10;

rinsing of the membrane twice for 5 min with T.TBS and once for 5 min with TBS;

the antigen-antibody complex is developed by bringing the membrane into contact with a developing buffer containing 4-chloro-1-naphthol in diethylene and hydrogen peroxide;

rinsing of the membrane with water.

Results

Analysis of the immunoblotting shows the presence of several additional bands for the induced sample not treated with endoglycosidase H compared with the non-induced sample, the two main additional bands corresponding to an apparent molecular weight of 9±2 and 11±2 kDa. These two bands are recognized by the immune serum. Diffuse bands with an apparent molecular weight of more than 16±2 kDa are also detected.

In the induced sample, the diffuse bands corresponding to a molecular weight of more than 16±2 kDA tend to disappear after treatment with endoglycosidase H in favor of a band with an apparent molecular weight of 16±2 kDa which may correspond to the precursor retaining the pro-sequence of the pheromone. In this same treated sample, it is noted that the two main bands with apparent molecular weights of 9±2 and 11±2 kDa are still present.

In the induced sample, the band corresponding to an apparent molecular weight of 11±2 kDa tends to disappear after treatment with α-mannosidase, whereas the band of 9±2 kDa increases in intensity under the same conditions. This seems to indicate that the protein corresponding to an apparent molecular weight of 11±2 kDa is O-glycosylated.

Table 2

Composition and Preparation of Certain Media Used to Prepare the Samples uracil-free liquid medium with glucose:

6.7 g of yeast nitrogen base without amino acids (from Difco)

5.0 g of casein hydrolysate (casamino acids from Difco)

10.0 g of glucose

Mix all the ingredients in distilled water and make up to a final volume of 1 l with distilled water. Autoclave for 10 min at 120° C.

uracil-free liquid medium with ethanol, glycerol and galactose:

Use the formulation of the uracil-free liquid medium described above, but without glucose. After autoclaving, add 10 ml of ethanol 100%, 30 g of glycerol and 30 g of galactose.

SECTION 9
Purification of Protein NC28 Produced in Yeast and Determination of its Amino-Terminal Sequence 1) Purification of the Majority Form of Protein NC28 Produced by Yeast The majority form of the recombinant protein with an apparent molecular weight of 9±2 kDa (cf. section 8–2)-a)) was isolated and purified from the culture medium obtained at the end of section 8-1), using a protocol comprising the following successive steps:

Ion exchange chromatography on a DEAE-SEPHAROSE® column (Pharmacia) equilibrated beforehand with a solution of Tris-HCl 50 mM pH 8.0. Under these operating conditions, the protein does not bind to the gel.

Affinity chromatography on a column of heparin SEPHAROSE® (Pharmacia) equilibrated beforehand with a solution of Tris-HCl 50 mM pH 8, using a linear gradient of 0 to 1 M NaCl in a solution of Tris-HCl 50 mM pH 8.0 as the eluent.

Dialysis of the fractions containing the recombinant protein (determined by electrophoretic analysis on polyacrylamide gel in the presence of SDS) against a solution of PBS.

2) Analysis of the Purified Protein a) Electrophoresis on Polyacrylamide Gel in the Presence of SDS Analysis by electrophoresis on polyacrylamide gel in the presence of SDS, and developing with silver nitrate, shows the presence of one intense band corresponding to an apparent molecular weight of 9±2 kDa and two bands of very low intensity corresponding to apparent molecular weights of 8±2 and 11±2 kDa. The purity of the recombinant protein corresponding to these three bands is greater than 90%.

b) Determination of the Amino-Terminal Sequence

The amino-terminal sequence is determined according to Edman's degradation principle (Kia-Ki Han et al., 1977, Biochimie, 59, 557). The first amino-terminal amino acid is coupled with phenyl isothio-cyanate (PITC) and then cleaved. The derivative obtained is converted to a stable phenylthiohydantoin/amino acid absorbing at 269 nm. The product of each cycle is analyzed by HPLC.

The three amino-terminal sequences below are detected in respective proportions of 70%, 20% and 10%:

sequence 1: (amino acids 1–7 of SEQ ID NO:2) Gln Pro Val Gly Ile Asn Thr sequence 2: (amino acids 3–7 of SEQ ID NO:2) Val Gly Ile Asn Thr sequence 3: (amino acids 19–23 of SEQ ID NO:2) Lys Ile Pro Lys Gln Sequence 1 is the expected amino-terminal sequence, namely that of the mature protein of 76 amino acids (cf. FIG. 2) described in section 4, the coding sequence of which is introduced into vector pEMR617 described in section 7.

Sequences 1 and 2 (amino acids 1–7 and 3–7, respectively, of SEQ ID NO:2) are the amino-terminal sequences of the mature protein of 76 amino acids cleaved in its amino-terminal part of 2 and 18 amino acids respectively.

SECTION 10
Synthesis of Peptides and Production of Immune Sera

1) Synthesis of Peptides

Several peptides were synthesized, either manually by the so-called tea bag method described by Houghten, 1985, Proc. Natl. Acad. Sci. U.S.A., 82, 5131, or by a method using a Milligen synthesizer. In the first method, the synthesis support is enclosed in a solvent-resistant permeable envelope; thus the common synthesis steps (activations, washes, etc.) can be carried out simultaneously for a large number of peptides. The second method makes it possible to carry out a completely automated synthesis. In both cases, the synthetic chemistry is that commonly used for solid phase peptide synthesis (Merrifield et al., 1963, J. Am. Chem. Soc., 85, 2149–2154). In this method, the carboxy-terminal residue of the peptide to be synthesized is attached to an insoluble polymer and different amino acids are then added. The polypeptide chain increases in size in the amino-terminal direction. After the synthesis, the peptide is separated from the support with hydrofluoric acid and recovered in solution.

The first method was used to synthesize the peptides corresponding to amino acids 90–109, 94–109 and 97–109 (amino acids 57–76, 61–76 and 64–76 of SEQ ID No 16, respectively of the translated protein NC28 (SEQ ID NO:16) (cf. FIG. 2), which are called peptide C20, peptide C16 and peptide C13 respectively. The peptide corresponding to amino acids 48–69 (amino acids 15–36 of SEQ ID No 16) of the protein translated from NC28 cDNA (SEQ ID NO:16), called peptide 48–69, was synthesized automatically. All the peptides were purified by HPLC and determination of the amino acid composition and sequencing of the peptide were carried out on the purified products.

Analysis of the amino acid composition is entirely automated. The amino acid analyzer (model 420A, Applied Biosystems) effects hydrolysis followed by derivatization of the amino acids released. The derivatized amino acids are separated by a Brownlee 130A HPLC system connected in line with the 420A system.

The amino-terminal sequence is determined according to Edman's degradation principle. The first amino-terminal amino acid is coupled with phenyl iso-thiocyanate (PITC) and then cleaved. The derivative obtained is converted to a stable phenylthiohydantoin/ amino acid absorbing at 254 nm. The product of each cycle is analyzed by HPLC.

2) Preparation of Immune Sera

To produce immune sera, peptide 48–69 is coupled with a protein carrying the hemocyanin of Fisurella (KLH) by its carboxy-terminal cysteine residue using m-maleimidobenzoyl-N-hydroxysuccinimide ester (MBS) as the coupling agent.

Rabbits (New Zealand, male, about 2 kg) are immunized with the conjugate peptide 48-69/ KLH (amount corresponding to 800 µg of peptide) (rabbit no. 43) or with 50 µg of protein NC28 (purified from yeast—section 9) (rabbit no. 44) every two weeks according to the protocol described by Vaitukaitis, 1981, Methods in Enzymology, 73, 46. For the first injection, one volume of antigenic solution is emulsified with one volume of Freund's complete adjuvant (Sigma— ref. 4258). The booster doses (3 for rabbit no. 43 and 6 for rabbit no. 44) are administered in Freund's incomplete adjuvant (Sigma—ref. 5506).

The immune sera obtained are capable of recognizing protein NC28 produced in yeast and in COS cells by immunodetection after electrophoresis on polyacrylamide gel in the presence of SDS.

SECTION 11
Demonstration of a Chemotactic Activity for Protein NC28 and the Carboxy-Terminal Peptides Thereof
1) Method Used
a) Isolation of the Neutrophils Most of the erythrocytes are removed from peripheral blood by sedimentation at 37° C. for 30 min in a solution containing 0.6% of dextran T500 (Pharmacia—ref. 17-0320-01) and 0.09% of NaCl. The cells are subsequently deposited on top of a layer of FICOLL-PAQUE® (Pharmacia) and centrifuged at 400 g for 30 min. The peripheral blood mononuclear cells (PBMNC) are present at the interface between the FICOLL® and the supernatant, whereas the residual erythrocytes and the poly-nuclear cells (mainly neutrophils) are in the cell residue. This residue is resuspended in a solution of $NH_4Cl$ 0.8%, 10 mM Hepes and incubated at 37° C. for 7 min in order to burst the erythrocytes. The residual cells (mainly neutrophils) are centrifuged and washed in HBSS (Hanks' Balanced Salt Solution) buffer (Gibco BRL—ref. 041-04020 H), hereafter referred to as HBSS.

b) Isolation of the Monocytes

The principle of the isolation of monocytes has been described by A. Boyum, 1983, Scan. J. Immunol., 17, 429–436. It is summarized below. The method consists in separating the monocytes from the blood using the iodine-containing gradient medium NYCODENZ® (N,N'-bis(2,3-dihydroxypropyl)-5-[N-(2,3-dihydroxypropyl)acetamido]-2,4,6-triiodoisophthalamide). To accentuate the difference in density between the monocytes and lymphocytes, the osmolarity of the solution is increased so that the lymphocytes reject water and become denser. It is possible to use "NYCOPRED® 1.068" medium, which contains Nycodenz, sodium chloride and tricin/NaOH at optimal concentrations for the separation of monocytes (Nycomed Pharma AS, Norway—ref. 223510).

The Following Protocol is Used

Most of the erythrocytes are removed from peripheral blood by sedimentation at 37° C. for 30 min in a solution containing 0.6% of dextran and 0.09% of NaCl. The upper phase of the plasma, containing the monocytes, lymphocytes and neutrophils, is removed. To separate the monocytes from the other cells, tubes are prepared as follows: 6 ml of plasma are deposited on a layer of 3 ml of NYCOPRED® 1.068 (Nycomed Pharma AS, Norway—ref. 223510) in a tube of diameter 13–14 mm. After centrifugation at 600 g for 15 min, the clarified plasma is removed down to 3–4 mm above the interphase and the remainder of the plasma and all the NYCOPRED® solution are collected down to about 1 cm above the cell residue, whereby the lymphocytes are not removed.

The monocyte suspension collected is made up to a volume of 6–7 ml with a solution of the following composition: 0.9% NaCl, 0.13% EDTA, 1% BSA, and then centrifuged for 7 min at 600 g.

The monocytes are contaminated with platelets. The latter are removed by centrifugation followed by removal of the supernatant and resuspension with the same solution, these operations being repeated 3 times.

The cells are resuspended in RPMI 1640 medium (Gibco) containing 0.5% of bovine serum albumin (BSA).

c) Protocol for Demonstrating the Chemotaxis

The test used is the one described by W. Falk et al., 1980, J. Imm. Meth., 33, 239–247. The precise protocol used is explained below:

Boyden's chamber modified for the measurement of chemotaxis, marketed by Neuroprobe (ref. AP48), is used. The test samples, diluted in HBSS for the tests on the neutrophils and in RPMI medium containing 0.5% of BSA for the test on the monocytes, are placed in the wells in the lower plate. A polycarbonate filter (pore size: 5 mm; Nuclepore—ref. 155845) is laid on said plate with the shiny side down. The upper plate is laid on the filter. The cells (50,000 per 50 µl of buffer) are placed in the wells in the upper plate.

The chamber is incubated at 37° C. in a humidified oven or in a box containing wet cotton, for 1 h in the case of the test on the neutrophils and for 3 h in the case of the test on the monocytes. The filter is withdrawn and the cells which are on the dull side (cells which have not migrated) are removed by wiping the filter and scraping it with a rubber scraper, these last two operations being repeated once. The cells which have migrated are stained and fixed using the "Diff-quick" kit (Dade—ref. 130832). The number of cells on the shiny side of the filter (cells which have migrated) are counted under the microscope.

d) Preparation of the Samples
a) Samples of Recombinant Proteins protein NC28 derived from COS cells, purified as described in section 6.

protein NC28 derived from yeast, purified as described in section 9.

cytokinin MCP-1, obtained as follows: isolation of a plasmid pSE1 carrying the cDNA of cytokinin MCP-1 by screening the library prepared in section 2 using an oligonucleotide corresponding to part of the cDNA of cytokinin MCP-1, described by Yoshimura T. et al., 1989, Febs Lett., 244, 487–493, followed by transfection of the COS cells, culture of the transfected COS cells and purification of the cytokinin MCP-1, as described for protein NC28.

protein IL-8 (Endogen—ref. CY-09025).
b) Samples of Peptides

–peptide C13
–peptide C16     prepared as described in section 10
–peptide C20 peptide formyl-Met-Leu-Phe, generally called fMLP (Sigma—ref. F 3506)

Figure 6A:
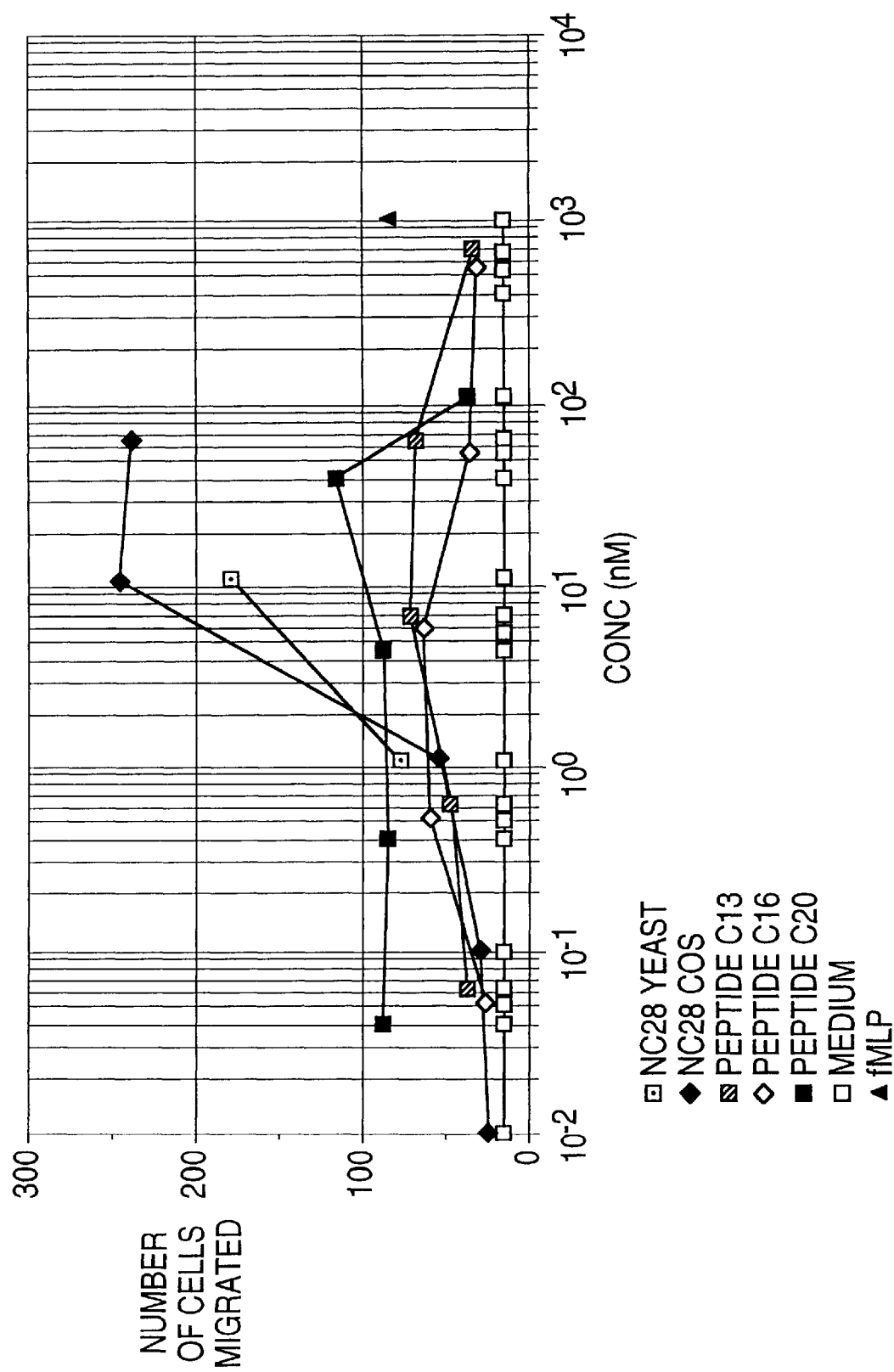
FIGS. 6a, 6b and 6c relate to the experiments for demonstrating the chemotactic activity.
Figure 6B:
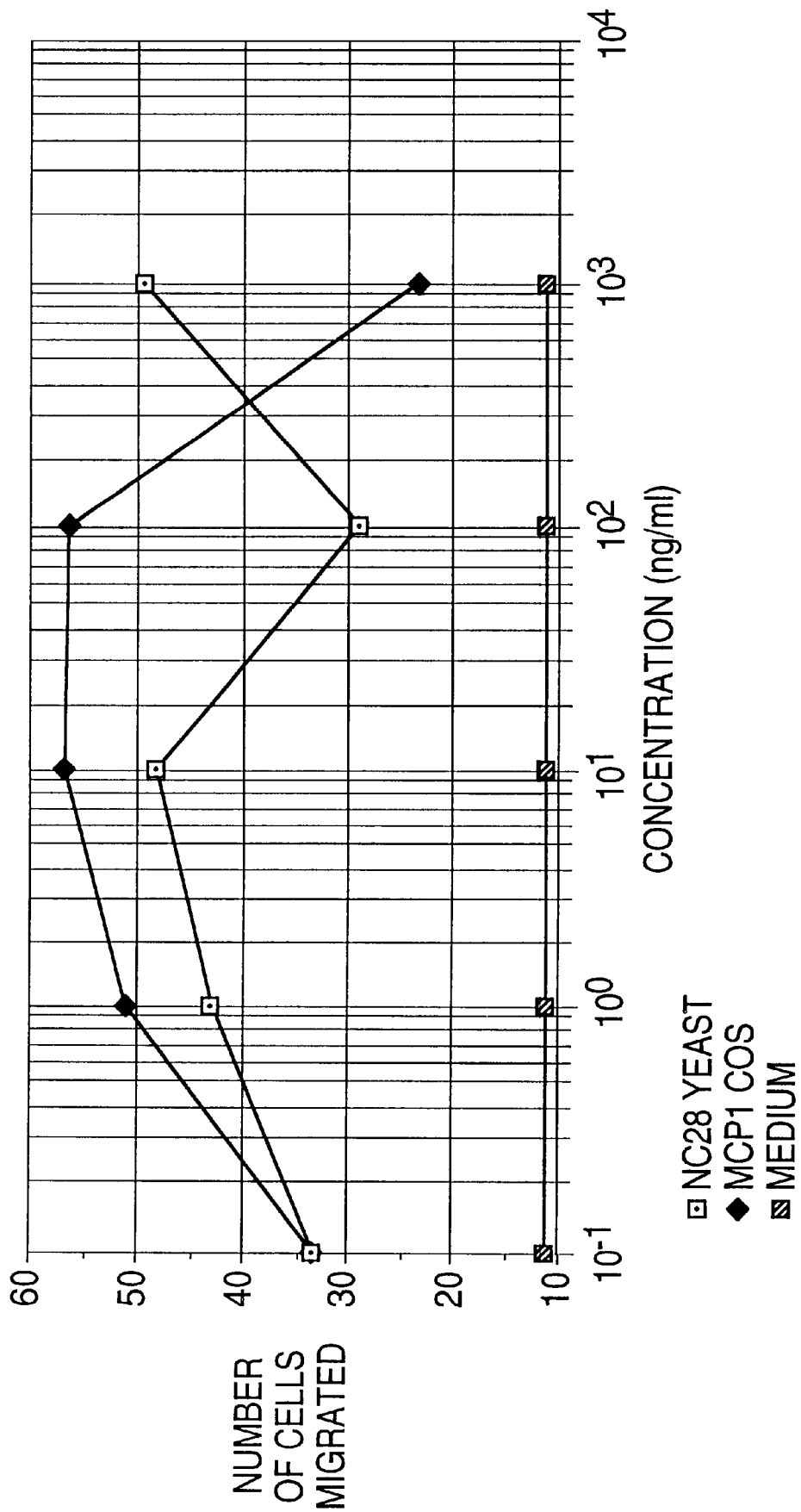

2) Results
a) Chemotaxis of Purified Protein NC28 Derived From COS Cells, and of Purified Protein NC28 Derived from Yeast, on Monocytes Some of the results obtained are illustrated in FIG. 6a, which shows the number of cells per microscopic field as a function of the concentration expressed in nM for purified protein NC28 derived from yeast, purified protein NC28 derived from COS cells and peptides C13, C16, C20 and fMLP, and in FIG. 6b, which shows the number of cells per microscopic field as a function of the concentration expressed in ng/ml for purified protein NC28 derived from yeast and purified cytokinin MCP-1 derived from COS cells.

FIG. 6a shows that, after 3 h of incubation, purified protein NC28 derived from yeast and purified protein NC28 derived from COS cells have a chemotactic activity on monocytes which is markedly greater than that of fMLP, a peptide which is known to possess a chemotactic activity on monocytes (Schiffmann E. et al., J. Immunol., 114, 1831). The carboxy-terminal peptides of protein NC28 also possess this activity.

FIG. 6b shows that the chemotactic activity of protein NC28 on monocytes is of the same order of magnitude as that of protein MCP-1, which is known for this activity (Rollins B. J. et al., 1991, Blood, 78, 1112), and that this activity is found at concentrations of 0.1 to 10 ng/ml.

b) Chemotaxis of Purified Protein NC28 Derived From Yeast, on Neutrophils

Figure 6C:
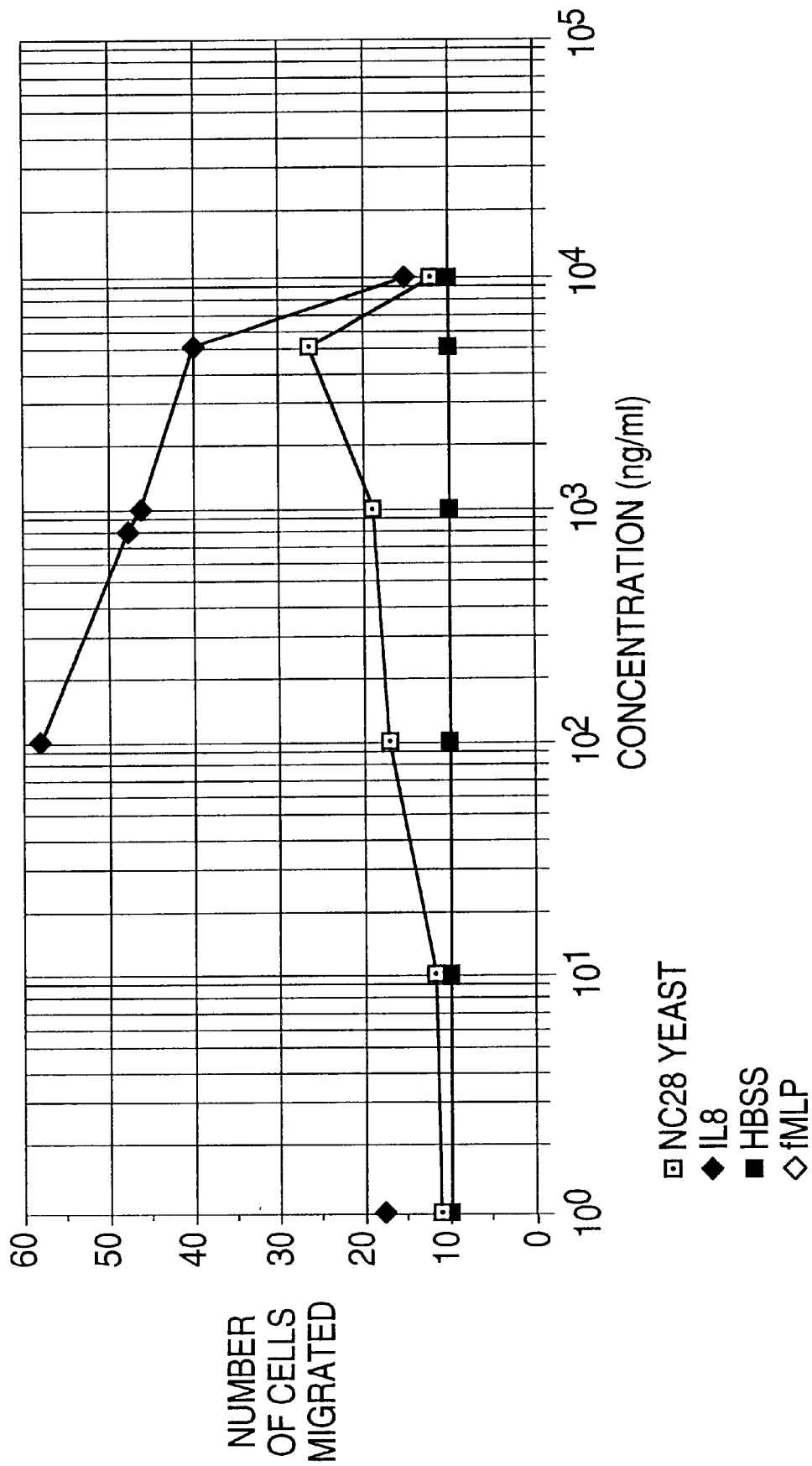

Some of the results obtained are illustrated in FIG. 6c, which shows the number of cells per microscopic field as a function of the concentration expressed in ng/ml for purified protein NC28 derived from yeast, cytokinin IL-8 and peptide fMLP.

It is found that protein NC28 has only a weak chemotactic activity on neutrophils (at high concentrations in excess of 100 ng/ml), in contrast to cytokinin IL-8 and peptide fMLP, both of which are known to possess this activity (Yoshimura T. et al., 1987, Proc. Natl. Acad. Sci. U.S.A., 84, 9233, 1, and Schiffman E. et al., 1975, J. Immunol., 114, 1831).

Protein NC28 is therefore a powerful and specific chemoattractant for monocytes.

What is claimed is:

1. An isolated protein that has chemotactic activity and that comprises the amino acid sequence of SEQ ID NO:1.

2. A protein according to claim 1, comprising amino acids 61–76 of SEQ ID NO:16.

3. A protein according to claim 2, comprising amino acids 57–76 of SEQ ID NO:16.

4. A protein according to claim 3, comprising amino acids 1–76 of SEQ ID NO:16.

5. A protein according to claim 4, wherein the N-terminus is blocked.

6. A protein according to claim 4 which has an apparent molecular weight, as determined by SDS-PAGE, of 9±2 kDa.

7. A protein according to claim 4 which has an apparent molecular weight, as determined by SDS-PAGE, of 11±2 kDa.

8. A protein according to claim 4 which has an apparent molecular weight, as determined by SDS-PAGE, of 16±2 kDa.

9. A protein according to claim 4, which is O-glycosylated.

10. A protein according to claim 4, which is N-glycosylated.

11. A protein according to claim 4, which has a degree of purity, as determined by SDS-PAGE, of more than 90%.

12. A protein according to claim 11, which has a degree of purity of more than 95%.

13. An isolated polynucleotide that encodes a chemotactic protein according to claim 1.

14. An isolated polynucleotide having a sequence fully complementary to the sequence of a polynucleotide according to claim 13.

15. A polynucleotide according to claim 13, wherein said chemotactic protein comprises the amino acid 1–76 of SEQ ID NO: 16.

16. A polynucleotide according to claim 13, wherein said chemotactic protein comprises the amino acid 57–76 of SEQ ID NO: 16.

17. A polynucleotide according to claim 13, wherein said chemotactic protein comprises the amino acid 61–76 of SEQ ID NO: 16.

18. A polynucleotide according to claim 13, wherein said chemotactic protein comprises a signal sequence.

19. A polynucleotide according to claim 18, wherein said signal sequence is SEQ ID NO: 7, 8, or 9.

20. A polynucleotide according to claim 19, wherein said signal sequence is encoded by a nucleotide sequence selected from the group consisting of SEQ ID NO: 10, 11, and 12.

21. A polynucleotide according to claim 15, comprising the sequence of SEQ ID NO: 13.

22. An expression vector that contains a polynucleotide according to claim 13 and the means necessary for its expression.

23. A cultured animal cell that contains a polynucleotide according to claim 13 and the means necessary for its expression.

24. A cultured animal cell according to claim 23, wherein said cell is a CHO cell.

25. A cultured animal cell according to claim 23, wherein said cell is a COS cell.

26. A yeast cell that contains a polynucleotide according to claim 13 and the means necessary for its expression.

27. A pharmaceutical composition that comprises the protein of claim 1 and a pharmaceutically acceptable carrier therefor.

28. A pharmaceutical composition that comprises the protein of claim 2 and a pharmaceutically acceptable carrier therefor.

29. A pharmaceutical composition that comprises the protein of claim 3 and a pharmaceutically acceptable carrier therefor.

30. A pharmaceutical composition that comprises the protein of claim 4 and a pharmaceutically acceptable carrier therefor.

31. An isolated polynucleotide that encodes a chemotactic NC28 polypeptide and that comprises a nucleotide sequence that is (a) the coding sequence of a cDNA molecule isolated from a human library, wherein the non-coding strand of the cDNA hybridizes, under the following conditions, to a probe having the sequence of SEQ ID NO: 15:
hybridize for two days at 42° C. in 50% formamide, 6×SSC, 5×Denhardt's solution, 0.1% SDS (following pre-hybridization in the same buffer);
wash several times at room temperature in 2×SSC, containing 0.1% SDS; and
wash twice for 15 minutes at 55° C. in 0.1×SSC, containing 0.1% SDS, or (b) a nucleotide sequence degenerate with the coding sequence of (a).

* * * * *

```
                          SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 13 amino acids
         (B) TYPE: amino acid
         (D) TOPOLOGY: linear (ii) MOLECULE TYPE: protein (xi) SEQUENCE DESCRIPTION: SEQ ID NO:1:

Met Lys His Leu Asp Lys Lys Thr Gln Thr Pro Lys Leu
1               5                  10

(2) INFORMATION FOR SEQ ID NO:2:

(i) SEQUENCE CHARACTERISTICS:
         (A) LENGTH: 63 amino acids
         (B) TYPE: amino acid
         (D) TOPOLOGY: linear (ii) MOLECULE TYPE: protein (xi) SEQUENCE DESCRIPTION: SEQ ID NO:2:

Gln Pro Val Gly Ile Asn Thr Ser Thr Thr Cys Cys Tyr Arg Phe Ile
1               5                  10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe
    50                  55                  60

(2) INFORMATION FOR SEQ ID NO:3:

(i) SEQUENCE CHARACTERISTICS:
         (A) LENGTH: 61 amino acids
         (B) TYPE: amino acid
         (D) TOPOLOGY: linear (ii) MOLECULE TYPE: protein (xi) SEQUENCE DESCRIPTION: SEQ ID NO:3:

Val Gly Ile Asn Thr Ser Thr Thr Cys Cys Tyr Arg Phe Ile Asn Lys
1               5                  10                  15

Lys Ile Pro Lys Gln Arg Leu Glu Ser Tyr Arg Arg Thr Thr Ser Ser
            20                  25                  30
```

```
His Cys Pro Arg Glu Ala Val Ile Phe Lys Thr Lys Leu Asp Lys Glu
        35                  40                  45

Ile Cys Ala Asp Pro Thr Gln Lys Trp Val Gln Asp Phe
    50                  55                  60
```

(2) INFORMATION FOR SEQ ID NO:4:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:4:

```
Lys Ile Pro Lys Gln Arg Leu Glu Ser Tyr Arg Arg Thr Thr Ser Ser
1               5                   10                  15

His Cys Pro Arg Glu Ala Val Ile Phe Lys Thr Lys Leu Asp Lys Glu
                20                  25                  30

Ile Cys Ala Asp Pro Thr Gln Lys Trp Val Gln Asp Phe
        35                  40                  45
```

(2) INFORMATION FOR SEQ ID NO:5:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:5:

```
Met Ala Pro Ser Gly Lys Ser Thr Leu Leu Leu Leu Phe Leu Leu Leu
1               5                   10                  15

Cys Leu Pro Ser Trp Asn Ala Gly Ala
                20                  25
```

(2) INFORMATION FOR SEQ ID NO:6:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Ser Pro Leu Lys Asn Ala Leu Val Thr Ala Met Leu Ala Gly
1               5                   10                  15

Gly Ala Leu Ser Ser Pro Thr Lys Gln His Val Gly Ile Pro Val Asn
                20                  25                  30

Ala Ser Pro Glu Val Gly Pro Gly Lys Tyr Ser Phe Lys Gln Val Arg
        35                  40                  45

Asn Pro Asn Tyr Lys Phe Asn Gly Pro Leu Ser Val Lys Lys Thr Tyr
    50                  55                  60

Leu Lys Tyr Gly Val Pro Ile Pro Ala Trp Leu Glu Asp Ala Val Gln
65                  70                  75                  80

Asn Ser Thr Ser Gly Leu Ala Glu Arg
                85
```

(2) INFORMATION FOR SEQ ID NO:7:

(i) SEQUENCE CHARACTERISTICS:
        (A) LENGTH: 23 amino acids

```
        (B) TYPE: amino acid
        (D) TOPOLOGY: linear (ii) MOLECULE TYPE: peptide (xi) SEQUENCE DESCRIPTION: SEQ ID NO:7:

Met Lys Ala Ser Ala Ala Leu Leu Cys Leu Leu Leu Thr Ala Ala Ala
1               5                   10                  15

Phe Ser Pro Gln Gly Leu Ala
            20

(2) INFORMATION FOR SEQ ID NO:8:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:8:

Met Pro Ser Pro Ser Asn Met Lys Ala Ser Ala Ala Leu Leu Cys Leu
1               5                   10                  15

Leu Leu Thr Ala Ala Ala Phe Ser Pro Gln Gly Leu Ala
            20                  25

(2) INFORMATION FOR SEQ ID NO:9:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:9:

Met Trp Lys Pro Met Pro Ser Pro Ser Asn Met Lys Ala Ser Ala Ala
1               5                   10                  15

Leu Leu Cys Leu Leu Leu Thr Ala Ala Ala Phe Ser Pro Gln Gly Leu
            20                  25                  30

Ala (2) INFORMATION FOR SEQ ID NO:10:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATGAAAGCCT CTGCAGCACT TCTGTGTCTG CTGCTCACAG CAGCTGCTTT CAGCCCCCAG          60

GGGCTTGCT                                                                  69

(2) INFORMATION FOR SEQ ID NO:11:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:
```

```
ATGCCCTCAC CCTCCAACAT GAAAGCCTCT GCAGCACTTC TGTGTCTGCT GCTCACAGCA        60

GCTGCTTTCA GCCCCCAGGG GCTTGCT                                           87
```

(2) INFORMATION FOR SEQ ID NO:12:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
ATGTGGAAGC CCATGCCCTC ACCCTCCAAC ATGAAAGCCT CTGCAGCACT TCTGTGTCTG        60

CTGCTCACAG CAGCTGCTTT CAGCCCCCAG GGGCTTGCT                              99
```

(2) INFORMATION FOR SEQ ID NO:13:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:13:

```
CAGCCAGTTG GGATTAATAC TTCAACTACC TGCTGCTACA GATTTATCAA TAAGAAAATC        60

CCTAAGCAGA GGCTGGAGAG CTACAGAAGG ACCACCAGTA GCCACTGTCC CCGGGAAGCT       120

GTAATCTTCA AGACCAAACT GGACAAGGAG ATCTGTGCTG ACCCCACACA GAAGTGGGTC       180

CAGGACTTTA TGAAGCACCT GGACAAGAAA ACCCAAACTC CAAAGCTT                    228
```

(2) INFORMATION FOR SEQ ID NO:14:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:14:

```
AGCTGGCTCG CATCTCTCCT TCACGCGCCC GCCGCCCTAC CTGAGGCCGC CATCCACGCC        60

GGTGAGTCGC GTTCTGCCGC CTCCCGCCTG TGGTGCCTCC TGAACTGCGT CCGCCGTCTA       120

GGTAGGCTCC AAGGGAGCCG GACAAAGGCC CGGTCTCGAC CTGAGCTCTA AACTTACCTA       180

GACTCAGCCG GCTCTCCACG CTTTGCCTGA CCCTGCTTGC TCAACTCTAC GTCTTTGTTT       240

CGTTTTCTGT TCTGCGCCGT TACAACTTCA AGGTATGCGC TGGGACCTGG CAGGCGGCAT       300

CTGGGACCCC TAGGAAGGGC TTGGGGGTCC TCGTGCCCAA GGCAGGGAAC ATAGTGGTCC       360

CAGGAAGGGG AGCAGAGGCA TCAGGGTGTC CACTTTGTCT CCGCAGCTCC TGAGCCTGCA       420

GA                                                                    422
```

(2) INFORMATION FOR SEQ ID NO:15:

(i) SEQUENCE CHARACTERISTICS:

(A) LENGTH: 814 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (ix) FEATURE:
          (A) NAME/KEY: CDS
          (B) LOCATION: 41..367

(ix) FEATURE:
          (A) NAME/KEY: mat_peptide
          (B) LOCATION: 140..367

(ix) FEATURE:
          (A) NAME/KEY: sig_peptide
          (B) LOCATION: 41..139

(xi) SEQUENCE DESCRIPTION: SEQ ID NO:15:

```
AGCAGAGGGG CTGAGACCAA ACCAGAAACC TCCAATTCTC ATG TGG AAG CCC ATG          55
                                            Met Trp Lys Pro Met
                                            -33         -30

CCC TCA CCC TCC AAC ATG AAA GCC TCT GCA GCA CTT CTG TGT CTG CTG        103
Pro Ser Pro Ser Asn Met Lys Ala Ser Ala Ala Leu Leu Cys Leu Leu
            -25                 -20                 -15

CTC ACA GCA GCT GCT TTC AGC CCC CAG GGG CTT GCT CAG CCA GTT GGG        151
Leu Thr Ala Ala Ala Phe Ser Pro Gln Gly Leu Ala Gln Pro Val Gly
        -10                 -5                   1

ATT AAT ACT TCA ACT ACC TGC TGC TAC AGA TTT ATC AAT AAG AAA ATC        199
Ile Asn Thr Ser Thr Thr Cys Cys Tyr Arg Phe Ile Asn Lys Lys Ile
  5              10                 15                  20

CCT AAG CAG AGG CTG GAG AGC TAC AGA AGG ACC ACC AGT AGC CAC TGT        247
Pro Lys Gln Arg Leu Glu Ser Tyr Arg Arg Thr Thr Ser Ser His Cys
             25                 30                 35

CCC CGG GAA GCT GTA ATC TTC AAG ACC AAA CTG GAC AAG GAG ATC TGT        295
Pro Arg Glu Ala Val Ile Phe Lys Thr Lys Leu Asp Lys Glu Ile Cys
            40                 45                  50

GCT GAC CCC ACA CAG AAG TGG GTC CAG GAC TTT ATG AAG CAC CTG GAC        343
Ala Asp Pro Thr Gln Lys Trp Val Gln Asp Phe Met Lys His Leu Asp
         55                  60                  65

AAG AAA ACC CAA ACT CCA AAG CTT TGAACATTCA TGACTGAACT AAAAACAAGC       397
Lys Lys Thr Gln Thr Pro Lys Leu
         70                  75

CATGACTTGA GAAACAAATA ATTTGTATAC CCTGTCCTTT CTCAGAGTGG TTCTGAGATT      457

ATTTTAATCT AATTCTAAGG AATATGAGCT TTATGTAATA ATGTGAATCA TGGTTTTTCT      517

TAGTAGATTT TAAAAGTTAT TAATATTTTA ATTTAATCTT CCATGGATTT TGGTGGGTTT      577

TGAACATAAA GCCTTGGATG TATATGTCAT CTCAGTGCTG TAAAAACTGT GGGATGCTCC      637

TCCCTTCTCT ACCTCATGGG GGTATTGTAT AAGTCCTTGC AAGAATCAGT GCAAAGATTT      697

GCTTTAATTG TTAAGATATG ATGTCCCTAT GGAAGCATAT TGTTATTATA TAATTACATA      757

TTTGCATATG TATGACTCCC AAATTTTCAC ATAAAATAGA TTTTTGTAAA AAAAAAA        814
```

(2) INFORMATION FOR SEQ ID NO:16:

(i) SEQUENCE CHARACTERISTICS:
          (A) LENGTH: 109 amino acids
          (B) TYPE: amino acid
          (D) TOPOLOGY: linear (ii) MOLECULE TYPE: protein (xi) SEQUENCE DESCRIPTION: SEQ ID NO:16:

```
Met Trp Lys Pro Met Pro Ser Pro Ser Asn Met Lys Ala Ser Ala Ala
-33             -30             -25             -20

Leu Leu Cys Leu Leu Leu Thr Ala Ala Ala Phe Ser Pro Gln Gly Leu
        -15             -10              -5

Ala Gln Pro Val Gly Ile Asn Thr Ser Thr Thr Cys Cys Tyr Arg Phe
 1               5              10                          15

Ile Asn Lys Lys Ile Pro Lys Gln Arg Leu Glu Ser Tyr Arg Arg Thr
             20              25                      30

Thr Ser Ser His Cys Pro Arg Glu Ala Val Ile Phe Lys Thr Lys Leu
             35              40              45

Asp Lys Glu Ile Cys Ala Asp Pro Thr Gln Lys Trp Val Gln Asp Phe
         50              55              60

Met Lys His Leu Asp Lys Lys Thr Gln Thr Pro Lys Leu
         65              70              75
```

(2) INFORMATION FOR SEQ ID NO:17:

(i) SEQUENCE CHARACTERISTICS:
        (A) LENGTH: 247 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
AGCTTGGATA AAAGACAGCC AGTTGGGATT AATACTTCAA CTACCTGCTG CTACAGATTT    60

ATCAATAAGA AAATCCCTAA GCAGAGGCTG GAGAGCTACA GAAGGACCAC CAGTAGCCAC   120

TGTCCCCGGG AAGCTGTAAT CTTCAAGACC AAACTGGACA AGGAGATCTG TGCTGACCCC   180

ACACAGAAGT GGGTCCAGGA CTTTATGAAG CACCTGGACA AGAAAACCCA AACTCCAAAA   240

CTTTGAG                                                             247
```

(2) INFORMATION FOR SEQ ID NO:18:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

```
AGCTTGTCGA CTAATACGAC TCACTATAGG GCGGCCGCGG GCCCCTGCAG GAATTCGGAT    60

CCCCCGGGTG ACTGACT                                                   77
```

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GATCCGGGCC CTTTTTTTTT TTT                                            23
```

(2) INFORMATION FOR SEQ ID NO:20:

-continued (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AAAAAAAAAA AAAGGGCCCG                                              20

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 6..38

(xi) SEQUENCE DESCRIPTION: SEQ ID NO:21:

ATCGA AGC TTG GAT AAA AGA CAG CCA GTT GGG ATT AAT AC              40
      Ser Leu Asp Lys Arg Gln Pro Val Gly Ile Asn
      1               5                   10

(2) INFORMATION FOR SEQ ID NO:22:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:22:

Ser Leu Asp Lys Arg Gln Pro Val Gly Ile Asn
1               5                   10

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CAGTGGATCC TCAAAGTTTT GGAGTTTGGG                                   30

(2) INFORMATION FOR SEQ ID NO:24:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO:24:

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

```
Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

(2) INFORMATION FOR SEQ ID NO:25:

(i) SEQUENCE CHARACTERISTICS:
        (A) LENGTH: 741 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
AACCGAGAGG CTGAGACTAA CCCAGAAAGA TCCAATTCTC AAACTGAAGC TCGCACTCTC      60

GCCTCCAGCA TGAAAGTCTC TGCCGCCCTT CTGTGCCTGC TGCTCATAGC AGCCACCTTC     120

ATTCCCCAAG GGCTCGCTCA GCCAGATGCA ATCAATGCCC CAGTCACCTG CTGTTATAAC     180

TTCACCAATA GGAAGATCTC AGTGCAGAGG CTCGCGAGCT ATAGAAGAAT CACCAGCAGC     240

AAGTGTCCCA AGAAGCTGT GATCTTCAAG ACCATTGTGG CCAAGGAGAT CTGTGCTGAC      300

CCCAAGCAGA AGTGGGTTCA GGATTCCATG GACCACCTGG ACAAGCAAAC CCAAACTCCG     360

AAGACTTGAA CACTCACTCC ACAACCCAAG AATCTGCAGC TAACTTATTT TCCCCTAGCT     420

TTCCCCAGAC ACCCTGTTTT ATTTTATTAT AATGAATTTT GTTTGTTGAT GTGAAACATT     480

ATGCCTTAAG TAATGTTAAT TCTTATTTAA GTTATTGATG TTTTAAGTTT ATCTTTCATG     540

GTACTAGTGT TTTTTAGATA CAGAGACTTG GGGAAATTGC TTTTCCTCTT GAACCACAGT     600

TCTACCCCTG GGATGTTTTG AGGGTCTTTG CAAGAATCAT TAATACAAAG AATTTTTTTT     660

AACATTCCAA TGCATTGCTA AAATATTATT GTGGAAATGA ATATTTTGTA ACTATTACAC     720

CAAATAAATA TATTTTGTA C                                                741
```